(12) United States Patent
Gonzalez et al.

(10) Patent No.: US 11,191,952 B2
(45) Date of Patent: *Dec. 7, 2021

(54) IMPLANTABLE THIN FILM DEVICES

(71) Applicant: PACESETTER, INC., Sylmar, CA (US)

(72) Inventors: John R. Gonzalez, McKinney, TX (US); Jeffrey Urbanski, Frisco, TX (US); Tommy Cushing, Prosper, TX (US)

(73) Assignee: PACESETTER, INC., Sylmar, CA (US)

( * ) Notice: Subject to any disclaimer, the term of this patent is extended or adjusted under 35 U.S.C. 154(b) by 169 days.

This patent is subject to a terminal disclaimer.

(21) Appl. No.: 16/278,464

(22) Filed: Feb. 18, 2019

(65) Prior Publication Data

US 2019/0175905 A1    Jun. 13, 2019

Related U.S. Application Data

(63) Continuation of application No. 15/265,594, filed on Sep. 14, 2016, now Pat. No. 10,207,103.

(Continued)

(51) Int. Cl.
*A61N 1/05*      (2006.01)
*H05K 3/18*      (2006.01)
(Continued)

(52) U.S. Cl.
CPC ........ *A61N 1/0551* (2013.01); *A61N 1/36071* (2013.01); *H05K 1/0298* (2013.01);
(Continued)

(58) Field of Classification Search
CPC .......... A61N 1/05; A61N 1/0551; A61N 1/36; A61N 1/36071; H05K 1/0298; H05K 1/09;
(Continued)

(56) References Cited

U.S. PATENT DOCUMENTS 4,890,623  A    1/1990   Cook et al.
6,208,881  B1   3/2001   Champeau
(Continued)

OTHER PUBLICATIONS

NonFinal Office Action, dated Dec. 13, 2017—parent U.S. Appl. No. 15/265,594.

(Continued)

*Primary Examiner* — Christopher A Flory
(74) *Attorney, Agent, or Firm* — Norton Rose Fulbright US LLP

(57) ABSTRACT

Implementations described and claimed herein provide thin film devices and methods of manufacturing and implanting the same. In one implementation, a shaped insulator is formed having an inner surface, an outer surface, and a profile shaped according to a selected dielectric use. A layer of conductive traces is fabricated on the inner surface of the shaped insulator using biocompatible metallization. An insulating layer is applied over the layer of conductive traces. An electrode array and a connection array are fabricated on the outer surface of the shaped insulator and/or the insulating layer, and the electrode array and the connection array are in electrical communication with the layer of conductive traces to form a flexible circuit. The implantable thin film device is formed from the flexible circuit according to the selected dialectic use.

22 Claims, 33 Drawing Sheets

Related U.S. Application Data

(60) Provisional application No. 62/358,428, filed on Jul. 5, 2016.

(51) Int. Cl.

| | | |
|---|---|---|
| *H05K 3/28* | (2006.01) | |
| *H05K 3/42* | (2006.01) | |
| *H05K 3/46* | (2006.01) | |
| *H05K 1/11* | (2006.01) | |
| *H05K 1/09* | (2006.01) | |
| *H05K 3/06* | (2006.01) | |
| *H05K 3/00* | (2006.01) | |
| *H05K 1/02* | (2006.01) | |
| *A61N 1/36* | (2006.01) | |

(52) U.S. Cl.
CPC ............... *H05K 1/09* (2013.01); *H05K 1/115* (2013.01); *H05K 3/0032* (2013.01); *H05K 3/0064* (2013.01); *H05K 3/064* (2013.01); *H05K 3/18* (2013.01); *H05K 3/28* (2013.01); *H05K 3/42* (2013.01); *H05K 3/4644* (2013.01); *H05K 3/4673* (2013.01); *H05K 1/11* (2013.01); *H05K 3/184* (2013.01); *H05K 2201/0141* (2013.01); *H05K 2201/0338* (2013.01); *H05K 2201/05* (2013.01); *H05K 2201/051* (2013.01); *H05K 2203/065* (2013.01)

(58) Field of Classification Search
CPC ........ H05K 1/115; H05K 1/11; H05K 3/0032; H05K 3/0064; H05K 3/064; H05K 3/18; H05K 3/184; H05K 3/28; H05K 3/42; H05K 3/4644; H05K 3/4673; H05K 2201/0141; H05K 2201/0338; H05K 2201/05; H05K 2201/051; H05K 2203/065

See application file for complete search history.

(56) References Cited

U.S. PATENT DOCUMENTS

| | | | | |
|---|---|---|---|---|
| 8,788,042 | B2 * | 7/2014 | Mercanzini | A61B 5/04001 |
| | | | | 607/45 |
| 8,788,064 | B2 * | 7/2014 | Mercanzini | A61N 1/37205 |
| | | | | 607/116 |
| 8,849,415 | B2 * | 9/2014 | Bedenbaugh | H01R 24/58 |
| | | | | 607/115 |
| 9,314,618 | B2 * | 4/2016 | Imran | A61N 1/0553 |
| 9,440,082 | B2 * | 9/2016 | Mercanzini | A61B 5/04001 |
| 9,474,894 | B2 * | 10/2016 | Mercanzini | A61N 1/0534 |
| 9,549,708 | B2 * | 1/2017 | Mercanzini | A61B 5/0536 |
| 9,572,985 | B2 * | 2/2017 | Mercanzini | A61N 1/37205 |
| 9,925,376 | B2 * | 3/2018 | Hartig | A61N 1/0551 |
| 10,207,103 | B2 * | 2/2019 | Gonzalez | H05K 1/0298 |
| 2004/0039434 | A1 | 2/2004 | Schrom et al. | |
| 2008/0027504 | A1 | 1/2008 | Bedenbaugh | |
| 2008/0140152 | A1 | 6/2008 | Imran et al. | |
| 2010/0211172 | A1 | 8/2010 | Bellamkinda et al. | |
| 2011/0207328 | A1 | 8/2011 | Speakman | |
| 2011/0237921 | A1 | 9/2011 | Askin, III et al. | |
| 2011/0275947 | A1 | 11/2011 | Feldman et al. | |
| 2011/0301665 | A1 | 12/2011 | Mercanzini et al. | |
| 2012/0065699 | A1 | 3/2012 | Bedenbaugh | |
| 2013/0030352 | A1 | 1/2013 | Seymour et al. | |
| 2013/0197424 | A1 | 8/2013 | Bedenbaugh | |
| 2014/0031750 | A1 | 1/2014 | Ordeig et al. | |
| 2014/0058197 | A1 | 2/2014 | Salahieh et al. | |
| 2014/0088391 | A1 * | 3/2014 | Leach | A61B 5/0031 |
| | | | | 600/347 |
| 2014/0088672 | A1 * | 3/2014 | Bedenbaugh | A61B 5/0478 |
| | | | | 607/116 |
| 2014/0091054 | A1 | 4/2014 | Brindley et al. | |
| 2014/0277258 | A1 * | 9/2014 | Mercanzini | A61N 1/0531 |
| | | | | 607/45 |
| 2014/0303703 | A1 * | 10/2014 | Mercanzini | A61N 1/0534 |
| | | | | 607/116 |
| 2015/0148877 | A1 | 5/2015 | Thakkar et al. | |
| 2015/0202351 | A1 * | 7/2015 | Kaplan | A61L 31/10 |
| | | | | 607/116 |
| 2015/0374990 | A1 * | 12/2015 | Fan | A61N 1/36046 |
| | | | | 607/54 |
| 2016/0059004 | A1 * | 3/2016 | Mercanzini | A61N 1/0534 |
| | | | | 607/116 |
| 2016/0059016 | A1 * | 3/2016 | Mercanzini | A61N 1/3787 |
| | | | | 607/60 |
| 2016/0066789 | A1 * | 3/2016 | Rogers | A61N 1/05 |
| | | | | 604/20 |
| 2016/0101280 | A1 | 4/2016 | Thakkar et al. | |
| 2016/0144078 | A1 * | 5/2016 | Young | A61L 31/026 |
| | | | | 600/378 |
| 2016/0144168 | A1 * | 5/2016 | Tol | G01R 33/288 |
| | | | | 607/45 |
| 2017/0252555 | A1 | 9/2017 | Greenberg et al. | |

OTHER PUBLICATIONS

Final Office Action, dated May 18, 2018—parent U.S. Appl. No. 15/265,594.

Notice of Allowance, dated Oct. 30, 2018—parent U.S. Appl. No. 15/265,594.

Corrected Notice of Allowability, dated Dec. 12, 2018—parent U.S. Appl. No. 15/265,594.

* cited by examiner

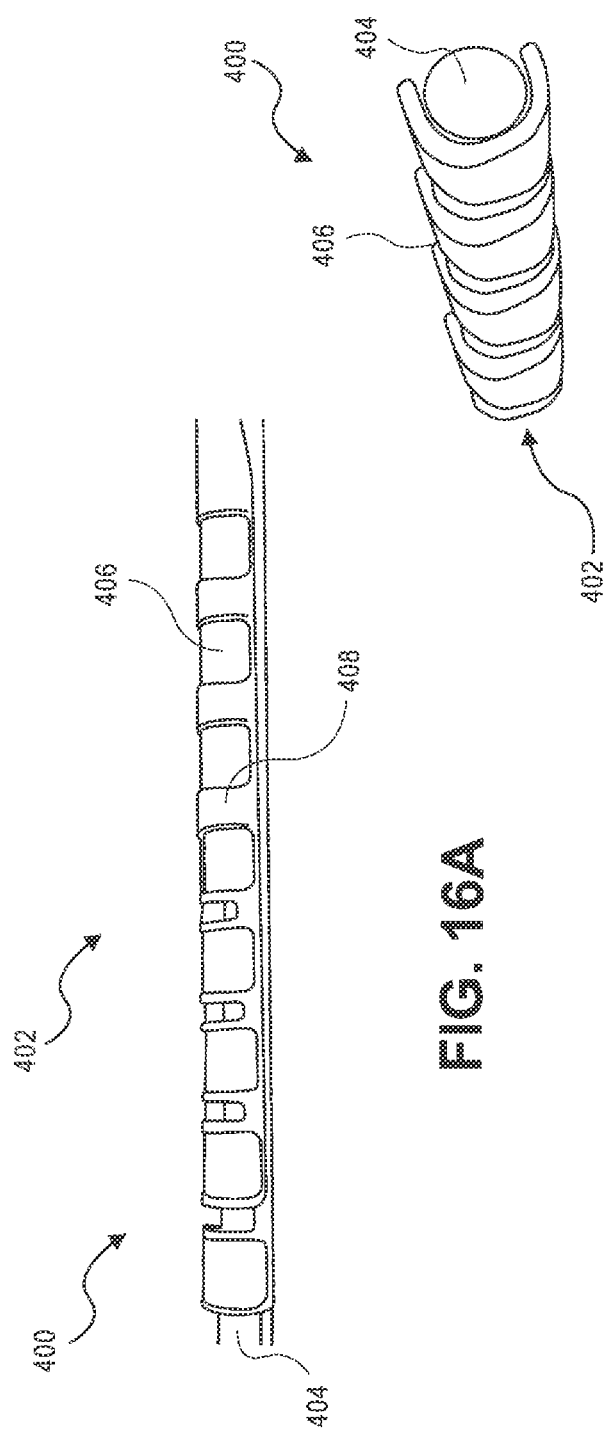
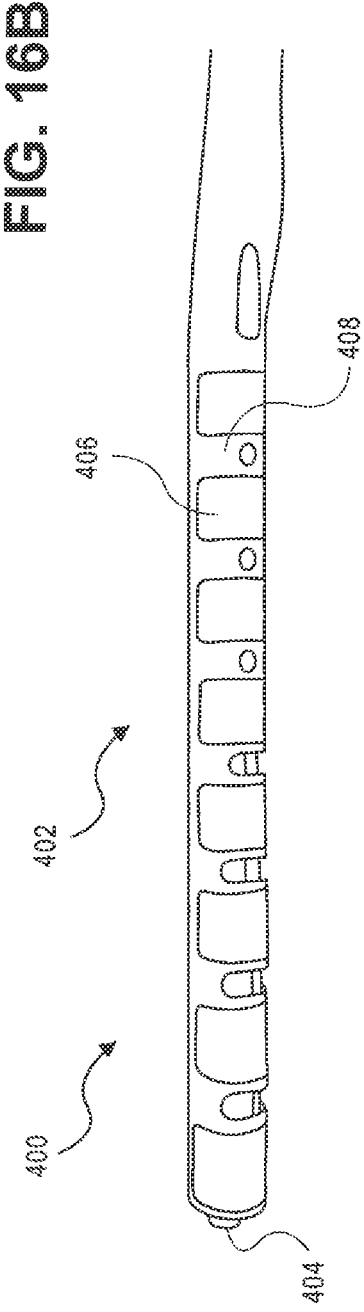
FIG. 16A
FIG. 16B
FIG. 16C

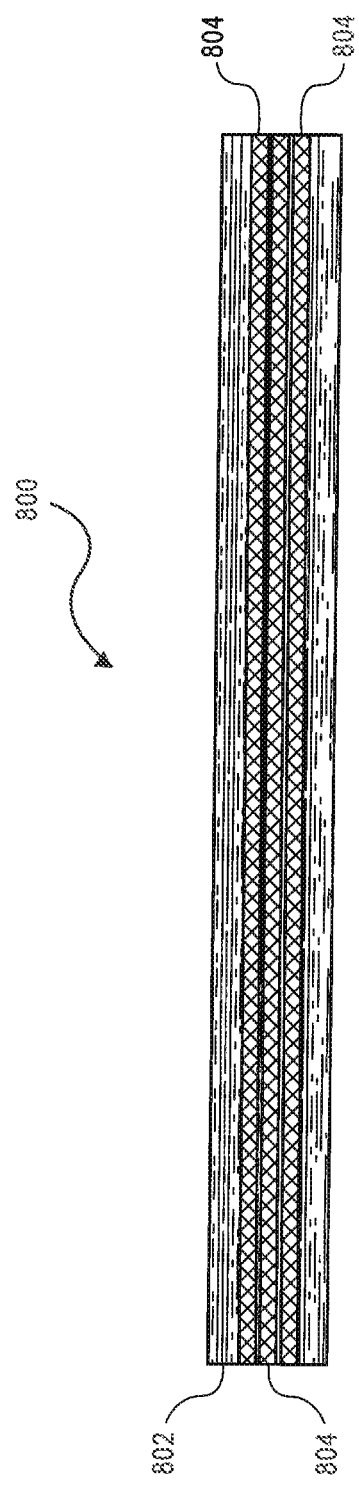

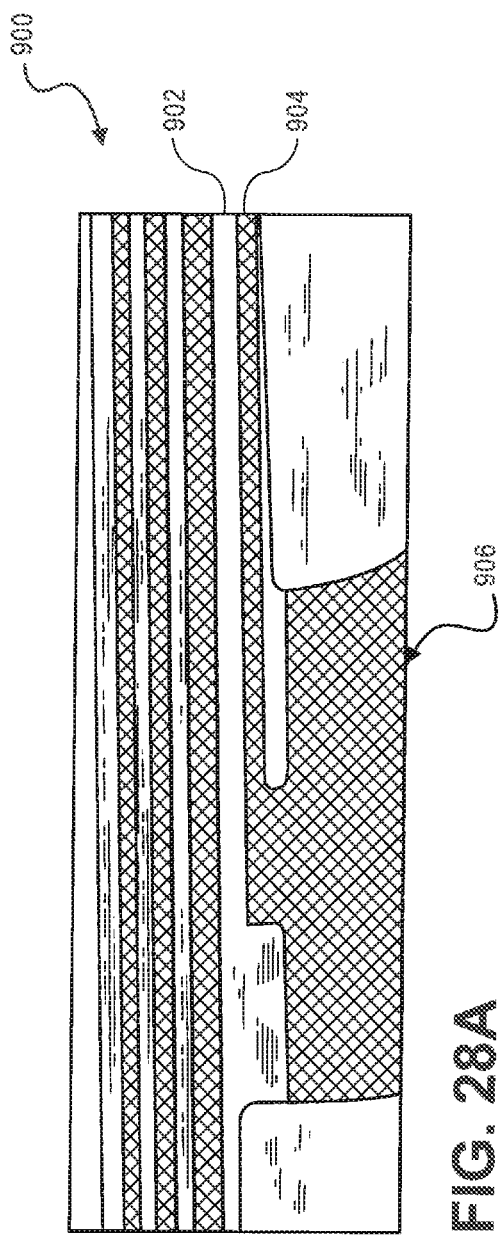
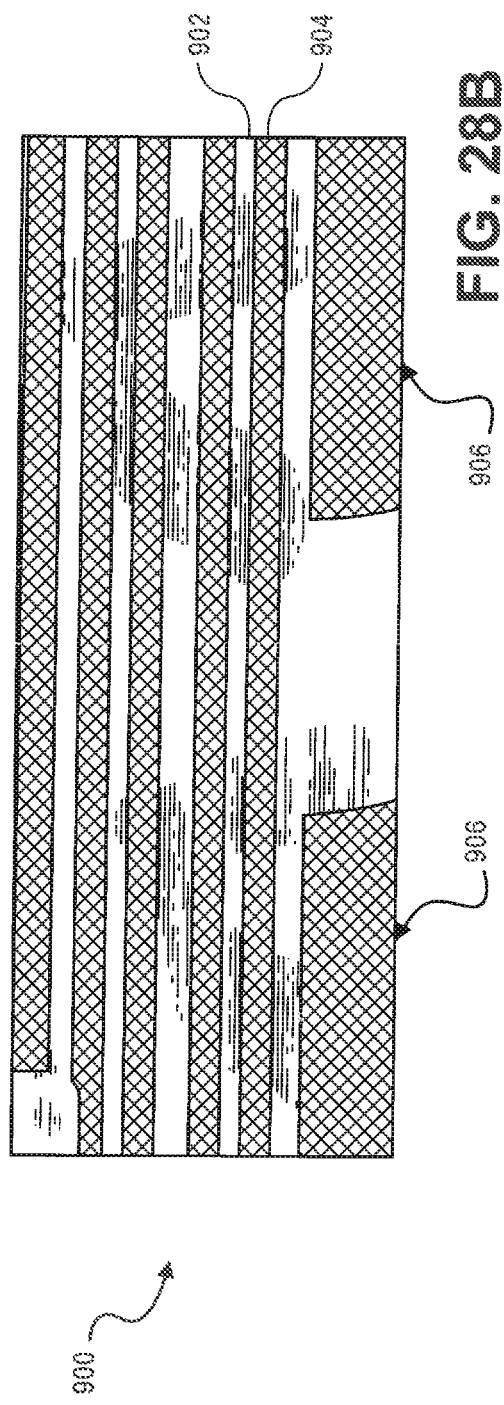

IMPLANTABLE THIN FILM DEVICES

CROSS REFERENCE TO RELATED APPLICATIONS

This application is a continuation of U.S. patent application Ser. No. 15/265,594, filed Sep. 14, 2016, which claims the benefit of U.S. Provisional Patent Application Ser. No. 62/358,428, filed Jul. 5, 2016, which are incorporated herein in their entirety.

TECHNICAL FIELD

Aspects of the present disclosure relate to thin film devices implantable in a patient for electrical stimulation of nerve or tissue and more particularly to thin film flexible circuits for implantable leads and other devices configured for various dielectric uses and deployment of thin film traces on a three-dimensional substrate.

BACKGROUND

Medical conditions may be treated through the application of electrical stimulation. For example, Spinal Cord Stimulation (SCS) involves driving an electrical current into particular regions of the spinal cord to induce paresthesia, which is a subjective sensation of numbness or tingling in a region of the body associated with the stimulated spinal cord region. Paresthesia masks the transmission of chronic pain sensations from the afflicted regions of the body to the brain, thereby providing pain relief to the patient. Typically, an SCS system delivers electrical current through electrodes implanted along the dura layer surrounding the spinal cord. The electrodes may be carried, for example, by a paddle lead, which has a paddle-like configuration with the electrodes arranged in one or more independent columns on a relatively large surface area, or percutaneous lead, which includes the electrodes arranged around a tube. Paddle leads are generally delivered into the affected spinal tissue through a laminectomy, involving the removal of laminar vertebral tissue to allow access to the dura layer and positioning of the paddle lead. Conventional delivery of paddle leads thus generally requires large incisions and substantial removal of lamina, resulting in trauma to the patient and longer procedure time. Similar challenges and disadvantages apply to other forms of leads implanted to treat other medical conditions through electrical stimulation. For example, implantable devices for Deep Brain Stimulation (DBS), catheter ablation, Cardiac Rhythm Management (CRM), Occipital nerve stimulation (ONS), Peripheral Nerve Stimulation (PNS), and the like are often plagued by such challenges and disadvantages. Further, conventional assembly procedures for electrically coupling a body to a lead and a pulse generator are often cumbersome, expensive, prone to breakage of conductive couplings, and/or result in pulse generators or other power sources with a large footprint. It is with these observations in mind, among others, that various aspects of the present disclosure were conceived and developed.

SUMMARY

Implementations described and claimed herein address the foregoing problems, among others, by providing implantable thin film devices and methods of manufacturing and implanting the same. In one implementation, a shaped insulator is formed having an inner surface and an outer surface. The shaped insulator has a profile shaped according to a selected dielectric use. A layer of conductive traces is fabricated on the inner surface of the shaped insulator using biocompatible metallization and defines a trace pattern. An insulating layer is applied over the layer of conductive traces with intimate contact between the inner surface of the shaped insulator and an inner surface of the insulating layer outside of the trace pattern. The insulating layer has an outer surface opposite the inner surface. An electrode array and a connection array are fabricated on at least one of the outer surface of the shaped insulator or the outer surface of the insulating layer, and the electrode array and the connection array are in electrical communication with the layer of conductive traces to form a flexible circuit. The implantable thin film device is formed from the flexible circuit according to the selected dialectic use.

In another implementation, an implantable thin film device for patient treatment comprises a shaped insulator having an inner surface and an outer surface. The shaped insulator has a profile shaped according to a selected dielectric use. A layer of conductive traces is disposed on the inner surface of the shaped insulator and defines a trace pattern. The layer of conductive traces is fabricated on the inner surface of the shaped insulator using biocompatible metallization. An insulating layer has an outer surface and an inner surface. The insulating layer is applied over the layer of conductive traces with intimate contact between the inner surface of the shaped insulator and the inner surface of the insulating layer outside of the trace pattern. An electrode array has one or more electrodes disposed on at least one of the outer surface of the shaped insulator or the outer surface of the insulating layer. A connection array has one or more connection spots disposed on at least one of the outer surface of the shaped insulator or the outer surface of the insulating layer. The electrode array and the connection array are in electrical communication with the layer of conductive traces to form a flexible circuit.

Other implementations are also described and recited herein. Further, while multiple implementations are disclosed, still other implementations of the presently disclosed technology will become apparent to those skilled in the art from the following detailed description, which shows and describes illustrative implementations of the presently disclosed technology. As will be realized, the presently disclosed technology is capable of modifications in various aspects, all without departing from the spirit and scope of the presently disclosed technology. Accordingly, the drawings and detailed description are to be regarded as illustrative in nature and not limiting.

BRIEF DESCRIPTION OF THE DRAWINGS

FIGS. 16A-16C illustrate a perspective view, a distal view, and a side perspective view, respectively, of an example stimulation end of a thin film lead wrapped around a biocompatible body.

FIG. 27 illustrates an example layer of conductive traces deployed on a three dimensional substrate.

FIGS. 28A and 28B each show an example layer of conductive traces and an electrode array deployed on a tube.

DETAILED DESCRIPTION

Figure 1:
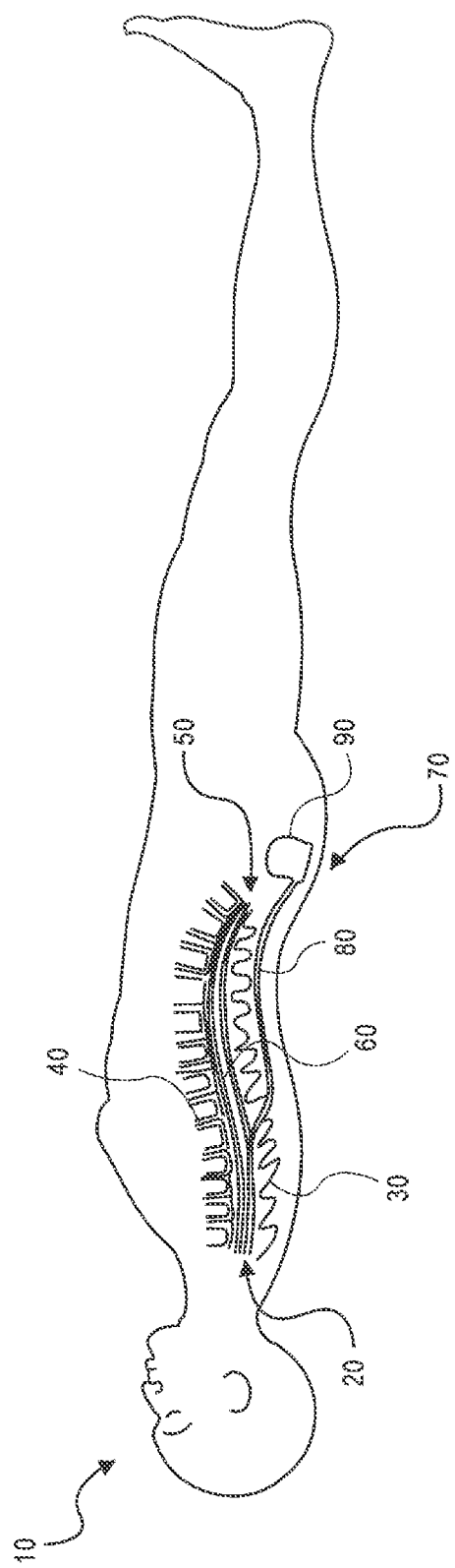
FIG. 1 shows a patient with an example thin film lead implanted for Spinal Cord Stimulation (SCS).

Aspects of the present disclosure involve thin film devices and methods of manufacturing and implanting the same. Generally, an implantable thin film device includes a flexible circuit formed from one or more layers with biocompatible metallization and a substrate, which may be two-dimensional (i.e., flat) or three-dimensional (i.e., non-flat). In one aspect, conductor traces are fabricated on a first insulating layer with biocompatible metallization, and a second insulating layer is applied over the conductor traces with intimate contact between the first insulating layer and the second insulating layer in contact areas outside of the conductor traces. After the conductor traces are encapsulated, vias may be formed in the first insulating layer and/or the second insulating layer and filled with conductive material. An electrode array and a connection array are fabricated on the first insulating layer and/or the second insulating layer and connected to the conductive material to form a flexible circuit, which may be a full tip-to-tail flexible circuit or flexible circuit tip assembly attached to a lead body.

The implantable thin film device is formed from the flexible circuit according to a selected dielectric use. Stated differently, the implantable thin film device may be formed by deploying the flexible circuit as is, laminating the flexible circuit to a flexible carrier, wrapping the flexible circuit around a body, and/or coiling the flexible circuit around a body. The implantable thin film device may thus be formed for surgical or percutaneous deployment across a variety of dielectric uses, including, without limitation, spinal cord stimulation (SCS), deep brain stimulation (DBS), catheter ablation, cardiac rhythm management (CRM), occipital nerve stimulation (ONS), peripheral nerve stimulation (PNS), electrophysiology (EP), atrial fibrillation (AF), vagus nerve, and the like.

In one aspect, where the implantable thin film device is formed for percutaneous deployment into a target location of a patient, a stylet, guidewire, or similar delivery structure may be integrated onto the flexible circuit or onto a flexible carrier to which the flexible circuit is laminated. Similarly, the flexible circuit may be deployed around such delivery structures, preloaded into a removable delivery sheath, or pulled to the target location in the patient with a custom stylet. Alternatively, a stylet may be loaded into a biocompatible tube around which the flexible circuit is wrapped or coiled for deployment.

Thus, the presently disclosed technology provides flexibility in manufacturing and deploying an implantable thin film device customized for a selected dielectric use and having a reduced footprint once implanted, among other advantages.

As described herein, the implantable thin film device may be formed for a selected dielectric use from one or more flexible circuits and Implanted into a target area of a patient. To begin a detailed description of an example of an implantable thin film lead formed and deployed for SCS treatment, reference is made to FIG. 1. It will be appreciated that while many of the example implementations described herein reference SCS treatment, the presently disclosed technology is applicable to other dielectric uses and may be customized accordingly.

Turning to FIG. 1, a patient 10 is treated for a medical condition through the application of electrical stimulation. In the example implementation shown in FIG. 1, the patient 10 is treated for chronic pain through SCS. In the vertebrate spinal column of the patient 10, the epidural/space 20 is positioned at the outermost part of the spinal canal formed by vertebrae 40, which have spinous process 30 projecting therefrom and providing a point of attachment for muscles and ligaments of the patient 10. Ligamentum flavum 50 connect the laminae of adjacent vertebrae 40. The lamina covers the spinal canal, which encloses and protects the spinal cord 60. In one implementation, an implantable stimulation system 70 includes an implantable thin film device 80 positioned at a target location in the epidural space 10 to drive an electrical current from a power source 90 into particular regions of the spinal cord 60 of the patient 10 to induce paresthesia. In this case, the implantable thin film device 80 is a thin film lead, and the power source 90 is an implantable pulse generator (IPG) or an external pulse generator (EPG). The thin film lead may be formed as a percutaneous lead or a paddle lead and deployed into the target location hi the epidural space 20 accordingly. As described herein, the footprint of the implantable stimulation system 70 within the patient 10 is minimized by customizing the implantable thin film device 80 according to a selected dielectric use, in this example, SCS.

In one implementation, the implantable thin film device 80 has a body extending between a proximal end and a distal end, which may be configured as a terminal end and a stimulation end, respectively. The terminal end of implantable thin film device 80 is configured to connect with the power source 90 to deliver power to the stimulation end, which is implanted in the target location of the patient 10. The stimulation end of the implantable thin film device 80 delivers electrical stimulation to the target location of the patient 10.

As described herein, the implantable thin film device 80 is formed from one or more flexible circuits according to the selected dielectric use, which may be, without limitation, SCS, DBS, CRM, ONS, PNS, EP, AF, catheter ablation, vagus nerve, or the like. Further, the implantable thin film device 80 may be formed from the one or more flexible circuits for percutaneous deployment or surgical deployment according to the selected dielectric use. For example, the implantable thin film device 80 may be formed from the flexible circuit(s) as a neurostimulation percutaneous lead configured for delivery through the skin of the patient 10 via a needle or as a neurostimulation paddle lead configured for surgical delivery, such as through a laminotomy operation in the case of SCS treatment. Generally, the one or more flexible circuits comprise a multiple layer design formed through biocompatible metallization and involving a flexible polymer or inorganic substrate.

In one implementation, the implantable thin film device 80 includes a full tip-to-tail flexible circuit having a stimulation end and a terminal end connected by a body. A length of the full tip-to-tail flexible circuit from which the implantable thin film device 80 is formed may vary according to the selected dielectric use. In one implementation, the length of the full tip-to-tail flexible circuit may range from approximately 12 to 80 inches depending on the selected dielectric use for the implantable thin film device 80. For example, the length may be approximately 12 to 36 inches where the implantable thin film device 80 is a neurostimulation lead and over approximately 72 inches where the implantable thin film device 80 is an ablation catheter or EP device. Further, a shape and profile of the implantable thin film device 80 may be formed from the flexible circuit based on the selected dielectric use. Where the implantable thin film device 80 is a neuromodulation percutaneous lead, the full tip-to-tail flexible circuit may be deployed cylindrically or flat, for example depending on a connection to the power source 90. More particularly, where the power source 90 is configured for a cylindrically shaped connector, the full tip-to-tail flexible circuit may be wrapped or coiled around a tube to form the terminal end of the implantable thin film device 80 as a cylindrically shaped connector, such that the terminal end of the implantable thin film device 80 may be connected directly into the power source 90 without an additional interface.

It will be appreciated that in alternative to the implantable thin film device 80 being formed from a full tip-to-tail flexible circuit, the one or more flexible circuits from which the implantable thin film device 80 is formed may include, without limitation, flexible circuit tip assemblies. Further, the presently disclosed technology is applicable to non-flexible active tip assemblies, lead connections, as well as various forms of percutaneous leads, surgical paddle leads, and other implantable devices.

To manufacture the implantable thin film device 80, in one implementation, a shaped insulator is formed from a substrate comprising one or more layers. The substrate may be made from an insulating material, including, without limitation, polyimide, organic thermoplastic polymer (e.g., Polyether ether ketone (PEEK)), liquid crystal polymer (LCP), flexible glass, flexible ceramic, rigid ceramic, and/or other insulating materials. The shaped insulator may be flexible, non-flexible (e.g., rigid), a combination of flexible and non-flexible, or transitionally stuff (e.g., transitioning or otherwise varying in stiffness from flexible to rigid along a length of the implantable thin film device 80). The shaped insulator of the implantable thin film device 80 has an inner surface and an outer surface extending along a length of the shaped insulator between a proximal end and a distal end. The outer surface is configured for contact with the tissue of the patient 10.

In one implementation, a profile of the shaped insulator defined transverse to a length of the inner surface and outer surface is shaped according to the selected dielectric use. For example, the selected dielectric use dictates formation parameters of the implantable thin film device 80, including, without limitation, stimulation direction (e.g., unidirectional stimulation or multi-directional stimulation), stimulation surface area, migration potential (e.g., extent to which longitudinal and lateral migration needs to be minimized after implant), deployment method (e.g., surgical or percutaneous), deployment shape (e.g., flat, cylindrical, etc.), connection to the power source 90 (e.g., a shape of the connection to the power source, etc.), and/or the like. As such, the profile of the shaped insulator is shaped accordingly, thereby facilitating deployment, minimizing a footprint of the implantable stimulation system 70 after implant, and customizing the implantable thin film device 80 for the selected dielectric use.

For example, a profile of the shaped insulator may be shaped for flat or cylindrical percutaneous deployment of the implantable thin film device 80. In one implementation, the shaped insulator is two-dimensional with the profile being flat to form the implantable thin film device 80 for flat percutaneous deployment. Similarly, the shaped insulator is three-dimensional with the profile being non-flat to form the implantable thin film device 80 for cylindrical percutaneous deployment. The non-flat profile may be curved, angled, and/or irregular. For example, in one implementation, the shaped insulator is a tube having a curved profile shape.

Once the shaped insulator is formed, a layer of conductive traces is fabricated on the inner surface of the shaped insulator using biocompatible metallization. The layer of conductive traces defines a trace pattern, in one implementation, the trace pattern includes one or more stimulation end traces, terminal end traces, and body traces. The stimulation end traces may be fabricated on the inner surface of the shaped insulator at the proximal end, the terminal end traces may be fabricated on the inner surface of the shaped insulator at the distal end, and the body traces may connect the terminal end traces to the stimulation end traces. Such a trace pattern may be defined, for example, where the flexible circuit is a full tip-to-tail flexible circuit. In another implementation, the trace pattern may include stimulation end traces or terminal end traces configured to connect with a wound lead body. Such a trace pattern may be defined, for example, where the flexible circuit is a flexible circuit tip assembly. The trace pattern will further be defined depending on the selected dielectric use, for example as it dictates an electrode count and deployment array, as discussed herein. Further, the trace pattern may include one or sub-patterns and/or variations between the stimulation end and the terminal end, thereby providing additional flexibility to the flexible circuit as defined for the selected dielectric use. For example, the trace pattern may include zig-zag patterns, linear patterns, angled patterns, contoured patterns, and/or the like. The trace pattern may vary along the stimulation end, the body, and the terminal end.

In one implementation, the biocompatible metallization includes metal deposition, foil attachment (e.g., laminated foils), conductive printing, and/or the like using one or more metals. The trace pattern may be defined using resist printing, ablation (e.g., laser ablation), etching, conductive printing, insulative impregnation, insulative implantation, and/or the like. For example, the layer of conductive traces may be fabricated using a fully biocompatible deposited or etched foil metal scheme. The metals may include, without limitation, Palladium (Pd), Gold (Au), Titanium (Ti), Platinum (Pt), Platinum-Iridium (Pt—Ir), metallic alloys comprising a plurality of these metals, and/or the like. It will be appreciated, however, that other biocompatible metals or non-metallic electrically conductive materials may be used. The biocompatible metallization may thus utilize seed deposition and plating, thin laminated foils for conductors, printed conductors, doped polymer traces, and/or the like.

Once the layer of conductive traces is fabricated on the shaped insulator, an insulating layer is applied to the shaped insulator over the layer of conductive traces. In one implementation, the insulating layer is applied with intimate contact between the inner surface of the shaped surface and an inner surface of the insulating layer outside the trace pattern. Stated differently, after application, there is intimate contact between the inner surface of the shaped insulator and the inner surface of the insulating layer where there are no traces, thereby encapsulating the layer of conductive traces between the shaped insulator and the insulating layer. The insulating layer may be made from an insulating material, including, without limitation, polyimide, organic thermoplastic polymer (e.g., PEEK), LCP, glass, ceramic, inorganic material, non-conductive oxide, thermoset polymer, and/or other flexible or rigid insulating materials. The insulating layer may be applied through extrusion, coating, casting, deposition, lamination, printing, and/or the like.

In one implementation, once the insulating layer is applied, the layer of conducting traces is encapsulated between the inner layer of the insulating layer and the inner layer of the shaped insulator, with the outer layer of the shaped insulator and an outer layer of the insulating layer configured to contact the tissue of the patient 10. In another implementation, the insulating layer and the layer of conductive traces are part of a multiple-layer series of alternating insulating and conducting layers. Stated differently, the implantable thin film device 80 may include conductive traces in a plurality of layers separated by insulating layers. The implantable thin film device 80 may thus include multiple layer traces and outer layer connections to support a higher trace count while minimizing the footprint of implantable stimulation system 70, among other advantages.

To deliver electrical stimulation to a target area of the patient 10 using the implantable thin film device 60, an electrode array having one or more electrodes and a connection array having one or more connection spots are fabricated on an outer surface of the shaped insulator and/or the outer surface of the insulating layer or outer surface of outermost insulating layer in the case of a multiple-layer series of alternating insulating and conducting layers. The electrode(s) and the connection spot(s) may be any two-dimensional shape (i.e., flat) or three-dimensional shape (i.e., non-flat). The three-dimensional shapes may include, without limitation, non-uniform spheres, spheres, polygons, and/or other curved and/or angled shapes.

In one implementation, the electrode array and the connection array are in electrical communication with the layer(s) of conductive traces to form a flexible circuit. Electrical communication between the layer(s) of conductive traces and the electrode array and the connection array may be established in a variety of manners. For example, in one implementation, one or more vias are formed in the outer surface of the shaped insulator and/or the insulating layer(s) and filled with conductive material to establish the electrical communication. The number of electrodes included hi the electrode array and the number of connection spots in the connection array, and thus the trace pattern, may vary depending on the selected dielectric use. Stated differently, the implantable thin film device 80 formed from the one or more flexible circuits includes configurable traces, electrodes, and contacts for one or more selected dielectric uses. The flexible circuit is thus not limited to a printed circuit board or silicon wafer scheme but can also utilize a roll to roll process, flat panel display process, and/or the like.

The flexible circuit may be, for example, a full tip-to-tail flexible circuit, a flexible circuit tip assembly, and/or the like. In one implementation, the flexible circuit is a full tip-to-tail flexible circuit having a stimulation end and a terminal end connected by body traces. The electrode array is disposed at the stimulation end and configured to deliver electrical stimulation to the target location in the patient 10, and the connection array is disposed at the terminal/end and configured to connect to the power source 90 to supply electrical energy to the electrode array via the one or more layers of conductive traces. In another implementation, the flexible circuit is a flexible, circuit tip assembly, for example configured as a stimulation end tip assembly. Here, the connection array is electrically connected to one or more conductors of a body (e.g., conductive wires of a lead body) to deliver electrical energy to the electrode array from the power source 90.

More particularly, where the layer of conductive traces is part of a flexible circuit tip assembly, for example a stimulation end tip assembly, each connection spot in the connection array may be aligned with and placed over a respective conductive wire of the body of the implantable thin film device 80. A laser may be used to weld each connection spot to the respective conductive wire of the body of the implantable thin film device 80. The connection array is in electrical communication with the electrode array through the layer of conductive traces, such that electrical energy may be delivered from the power source 90 through the conductive wires of the body of the implantable thin film device 80 to the target location of the patient 10. As such, the flexible circuits may be attached as Ups to a wound lead body to form the implantable thin film device 80.

The electrode array and the connection array of the implantable thin film device 80 may be fabricated using biocompatible metallization, including, but not limited to, metal deposition, foil attachment (e.g., laminated foils), conductive printing, and/or the like using one or more metals. The metals may include, without limitation, Pd, Au, Ti, Pt, and/or Pt—Ir. It will be appreciated, however, that other biocompatible metals or electrically conductive materials may be used. In one implementation, the biocompatible metallization used in fabricating the electrode array and the connection array is the same as the biocompatible metallization used in fabricating the one or more layers of conductive traces.

In one implementation, the biocompatible metallization of the layer of conductive traces, the electrode array, and/or the connection array involves laser ablation in manufacturing the implantable thin film device 80. A thin layer of biocompatible conductive metal, such as Pd, Au, Ti, Pt, Pt—Ir, and/or the like, is adhered or otherwise coupled to a surface of an insulator (e.g., the inner surface of the shaped insulator). The trace pattern of the layer of conductive traces is defined through the formation of separating trenches using a laser. More specifically, sufficient power is applied by the laser to ablate a portion of the thin layer of biocompatible conductive metal until each trace is electrically isolated from other traces in the trace pattern. The electrode array and/or the connection array may be similarly fabricated through laser ablation.

The implantable thin film device 80 is formed from one or more flexible circuits according to the selected dielectric use. As described herein, the implantable thin film device 80 may be a percutaneous dead having a stimulation end and a terminal end form from the flexible circuit. The flexible circuit may be a full tip-to-tail flexible circuit that is deployed flat or otherwise as is following the fabrication of the electrode array and the connection array. Similarly, the implantable thin film device 80 may be a paddle lead configured for percutaneous or surgical deployment and formed from a full tip-to-tail flexible circuit or from one or more flexible circuit tip assemblies.

The implantable thin film device 80 may further be formed from one or more flexible circuits according to the selected dielectric use by laminating the flexible circuit to a carrier (e.g., a flexible carrier, a rigid carrier, a transitionally stiff carrier (e.g., a carrier that transitions in stiffness from flexible to rigid), etc.), wrapping the flexible circuit around a biocompatible body, coiling the flexible circuit around a biocompatible body, and/or the like. The flexible carrier may be two-dimensional (i.e., flat) or three-dimensional (i.e., non-flat) and made from a variety of materials, such as a biocompatible polymer. The biocompatible body may be a tube, mandrel, or similarly shaped body and made from a biocompatible polymer, such as Bionate®, Carbosil®, or Optim®, and/or other polymers and/or biocompatible materials.

Thus, the implantable thin film device 80 is formed from one or more flexible circuits according to the selected dielectric use. For example, the implantable thin film device 80 may be formed into a neuromodulation eight channel device for SCS, a segmented DBS device, a single channel CRM device, a multi-channel CRM device, a cable harness for ablation catheters, and the like.

In one implementation, the implantable thin film device 80 is formed and deployed into the target location of the patient 10 according to the selected dielectric use. For percutaneous deployment, a stylet, guide wire, or the like may be integrated onto the flexible circuit from which the implantable thin film device 80 is formed or onto a flexible carrier to which the flexible circuit is laminated. Alternatively, the flexible circuit from which the implantable thin film device 80 is formed may be: deployed around a stylet, guide wire, or the like; preloaded into a removable delivery sheath; pulled to the target location in the patient 10 with a custom stylet; and/or the like. In one implementation, a stylet is loaded into a biocompatible body around which the flexible circuit is wrapped or coiled to form the implantable thin film device 80. For a non-limiting example of the implantable thin film device 80 formed from the flexible circuit(s) as a paddle lead for percutaneous deployment for SCS treatment, reference is made to FIGS. 2-7.

Figure 2:
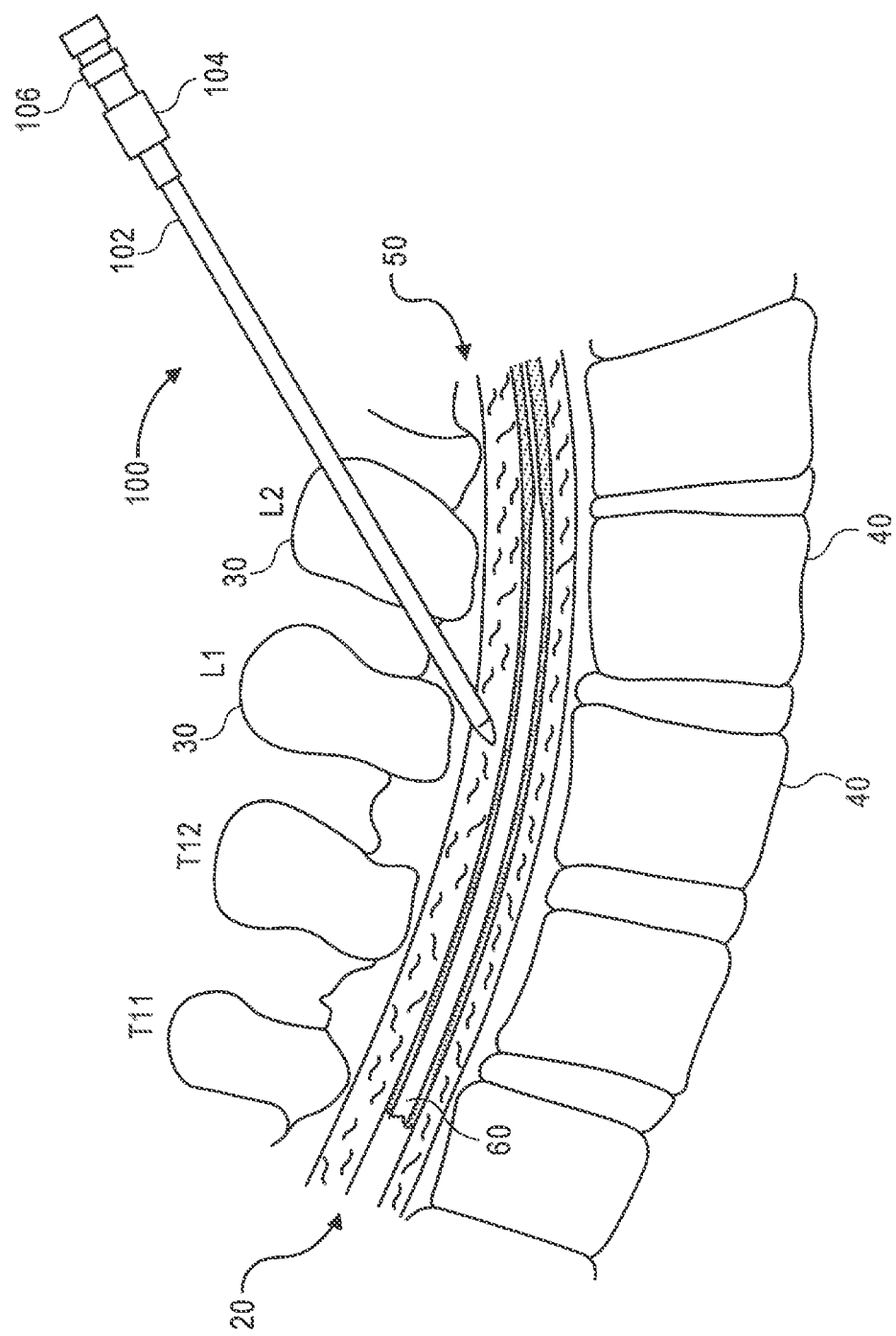
FIG. 2 shows an example deployment system and method for implanting a thin film paddle lead for SCS, the deployment system shown with a needle inserted into epidural space of the patient.

Turning first to FIG. 2, in one implementation, a target location in epidural space 20 of the patient 10 is chosen for positioning a stimulation end of the implantable thin film device 80 to deliver SCS treatment. The target location may be selected, for example, using fluoroscopy. Referring to FIG. 2, in one implementation, a deployment system 100 includes a needle 102, which is inserted through a small incision, for example, between the spinous processes 30 of two vertebrae 40. The needle 102 is advanced through subcutaneous tissue and the ligamentum flavum 50 of the spine into the epidural space 20 along the spinal cord 60. In one implementation, the needle 102 is inserted at an angle. Following entry of the needle 102 into the epidural space 20, an inner portion 106 (e.g., a stylet) is removed from a proximal end 104 of the needle 102.

Figure 3:
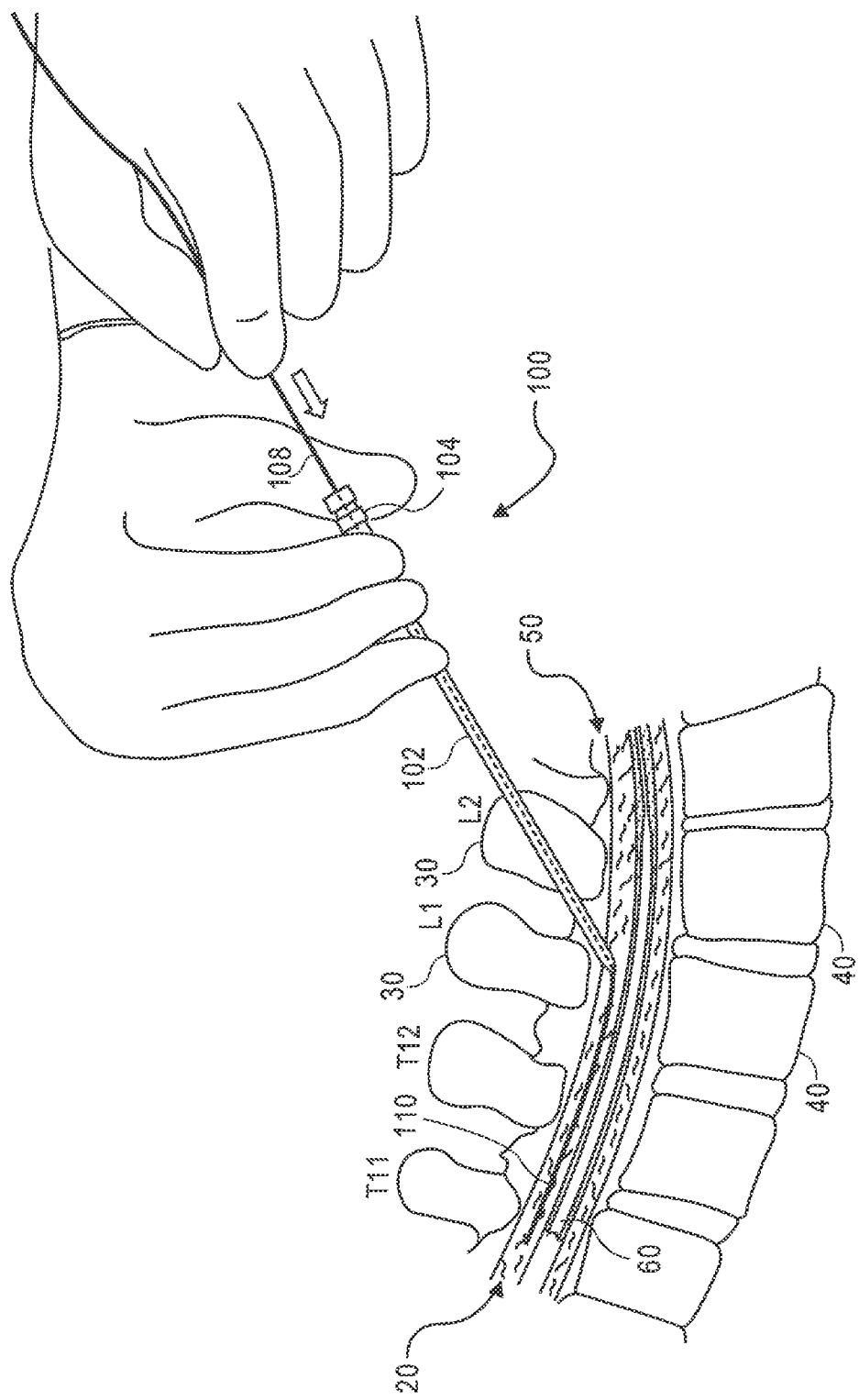
FIG. 3 illustrates the deployment system of FIG. 2 with a guide wire inserted through the needle into the epidural space of the patient.

Referring to FIG. 3, in one implementation, after removing the inner portion 106 from the needle 102, a guide wire 108 is inserted through the needle 102 into the epidural space 20. Fluoroscopy may be used to verify a position of a distal end 110 of the guide wire 108 in the target location of the epidural space 20. Once the distal end 110 of the guide wire 108 is positioned, the needle 102 is removed.

Figure 4:
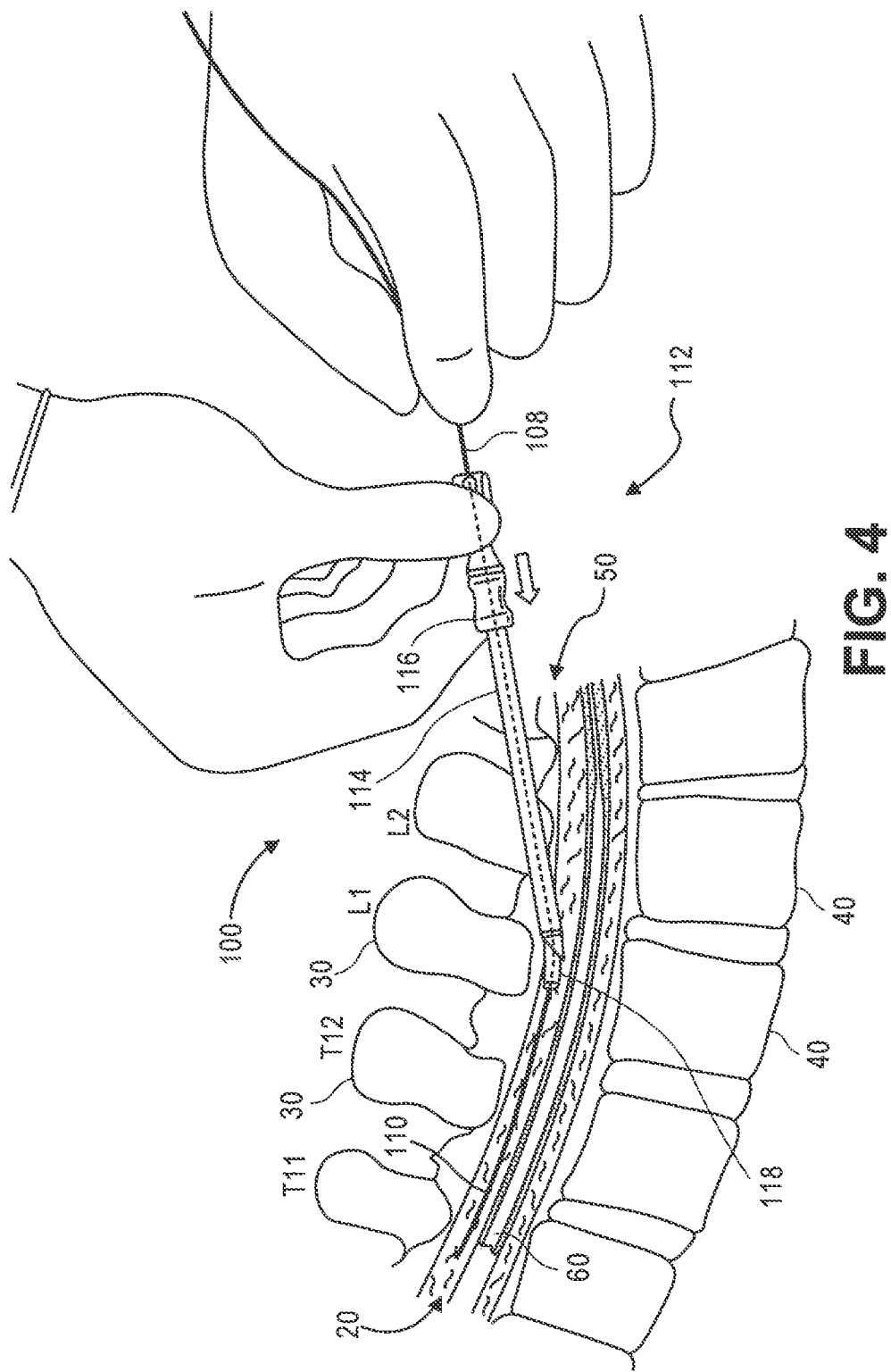
FIG. 4 illustrates the deployment system of FIG. 3 with a delivery tool inserted over the guide wire into the epidural space of the patient.
Figure 5:
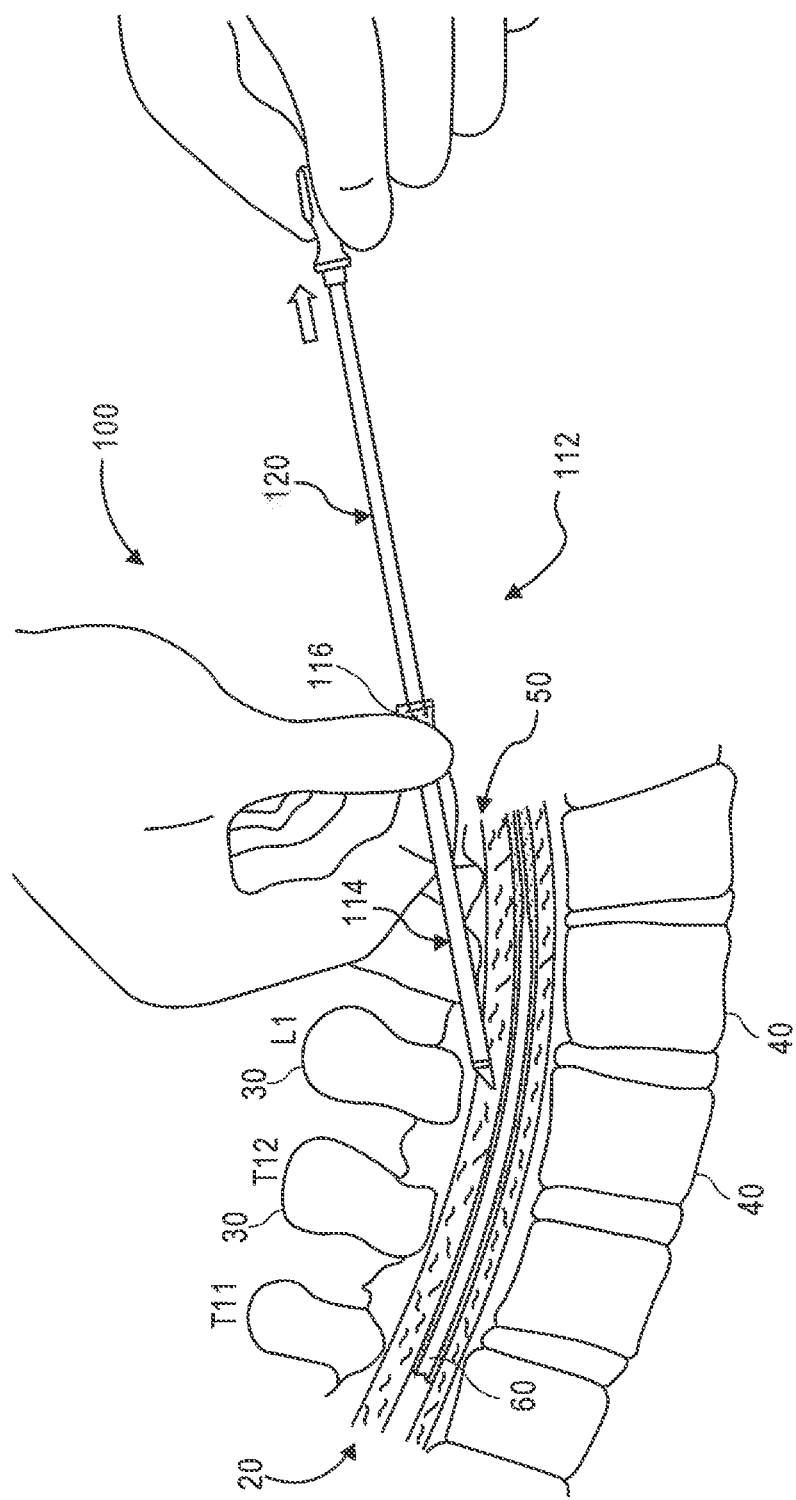
FIG. 5 shows the deployment system of FIG. 4 with an inner penetrator being removed from a sheath of the delivery tool.

As shown in FIG. 4, a delivery tool 112 having a sheath 114 extending from a hub 116 is deployed over the guide wire 108 into the epidural space 20. The delivery tool 112 may be inserted at an angle. In one implementation, as can be understood from FIGS. 4-5, a dilator 118 extends through a distal tip of the sheath 114 from an inner penetrator 120, permitting the delivery tool 112 to pass easily over the guide wire 188 without creating a false passage in an undesirable location of the anatomy of the patient 10. The dilator 118 may further provide indication to the surgeon of contact with the ligamentum flavum 50. Once the delivery tool 112 penetrates the ligamentum flavum 50, the guide wire 108 is removed, leaving the sheath 114 positioned in the epidural space 10. As shown in FIG. 5 in one implementation, the inner penetrator 120 is also removed.

Figure 6:
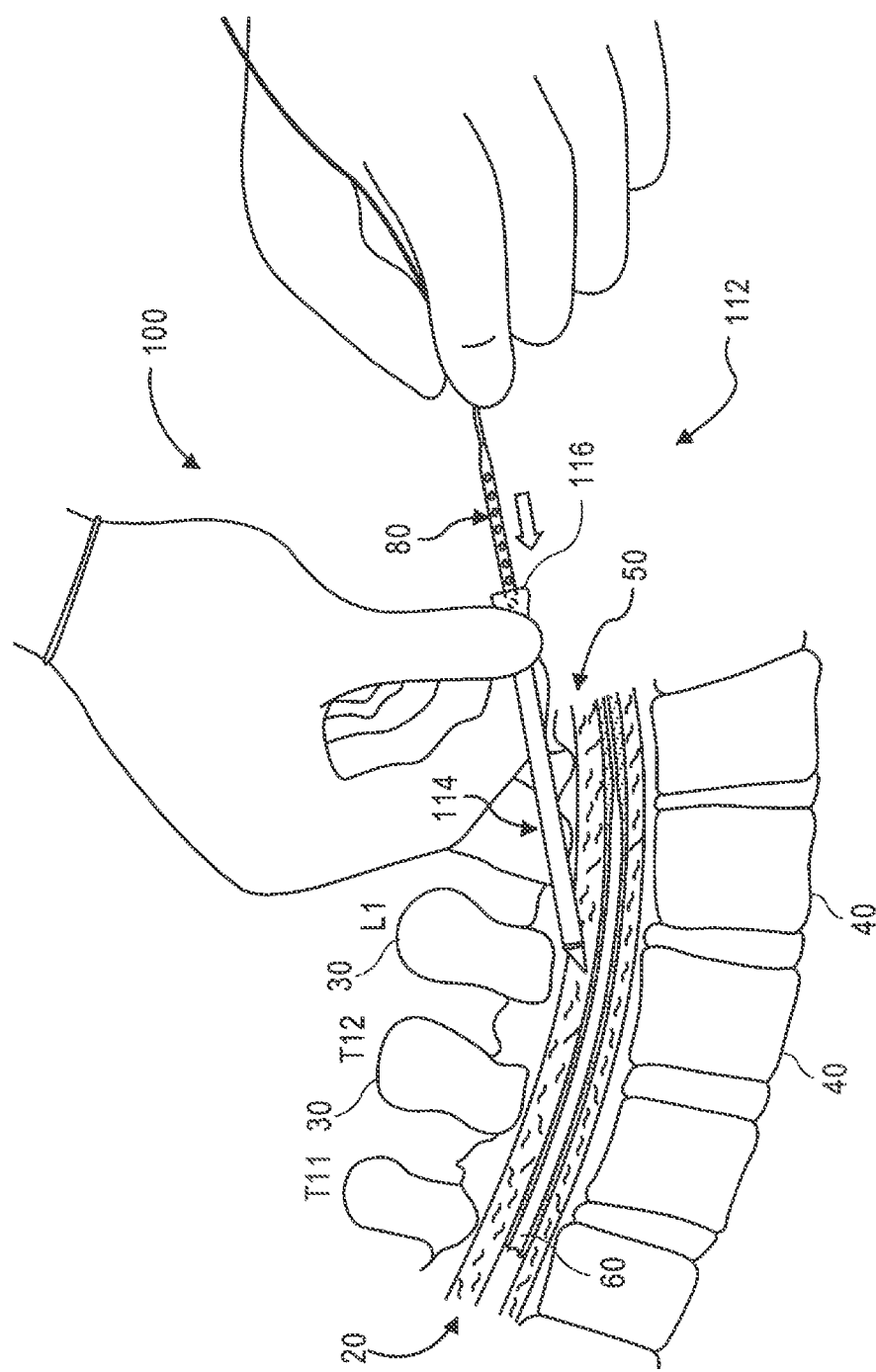
FIG. 6 illustrates the deployment system of FIG. 5 with the thin film paddle lead being inserted through the sheath of the delivery tool into the epidural space of the patient.
Figure 7:
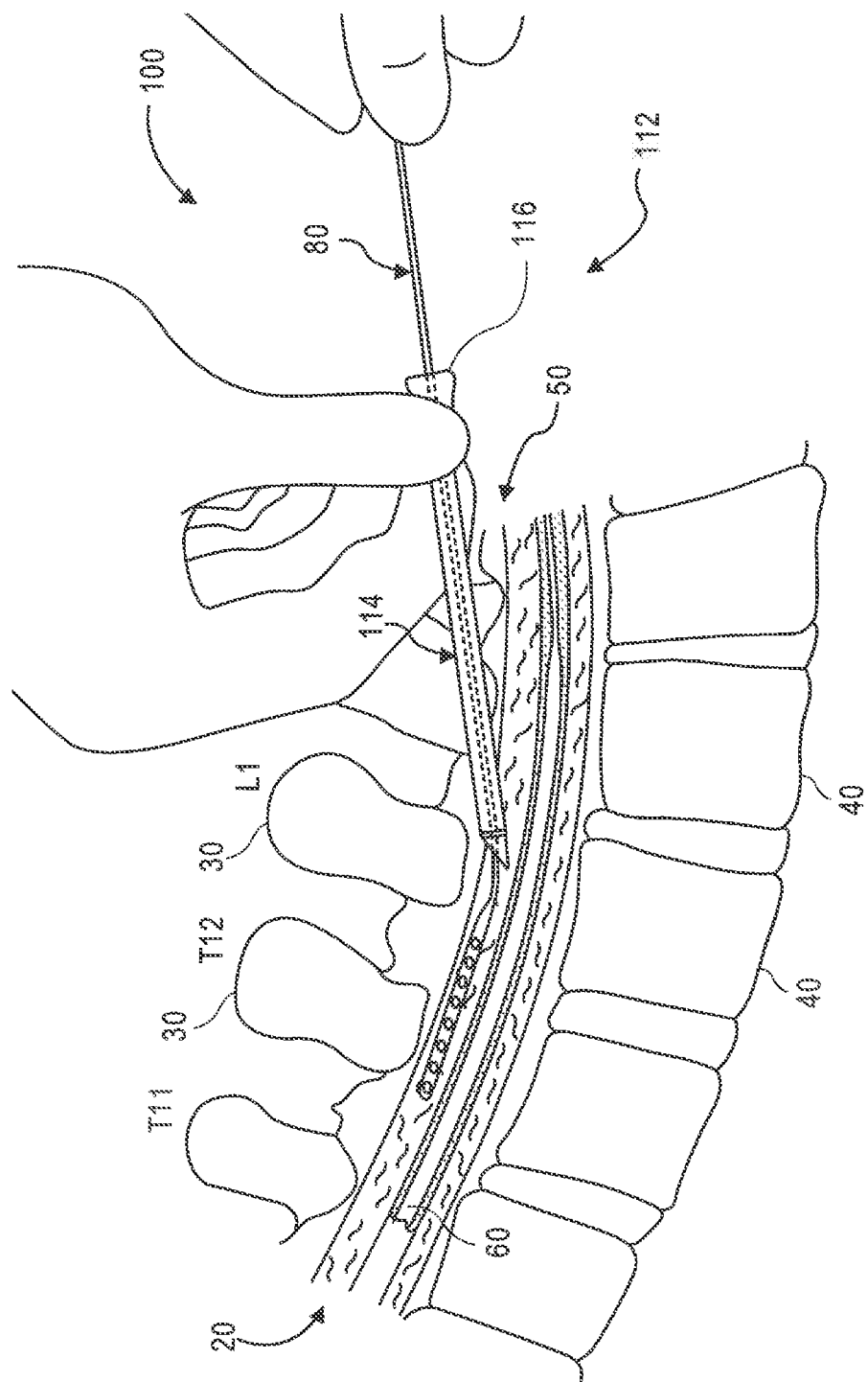
FIG. 7 illustrates the thin film paddle lead implanted and the delivery tool of the paddle lead deployment system of FIG. 6 being removed from the epidural space of the patient.
Figure 8:
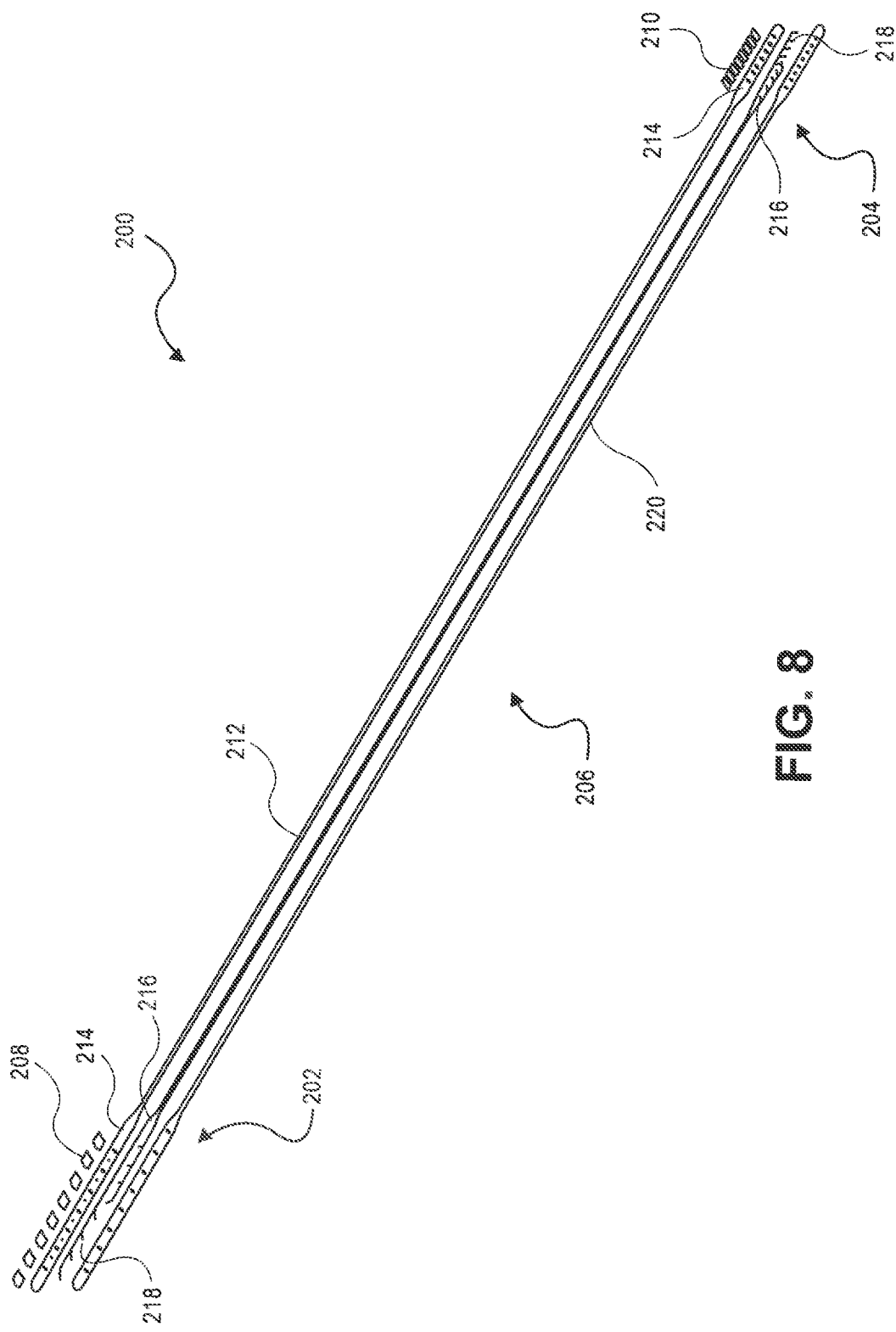
FIG. 8 is an exploded view of an example thin film lead, which may be wrapped radially around a mandrel or deployed flat.
Figure 9:
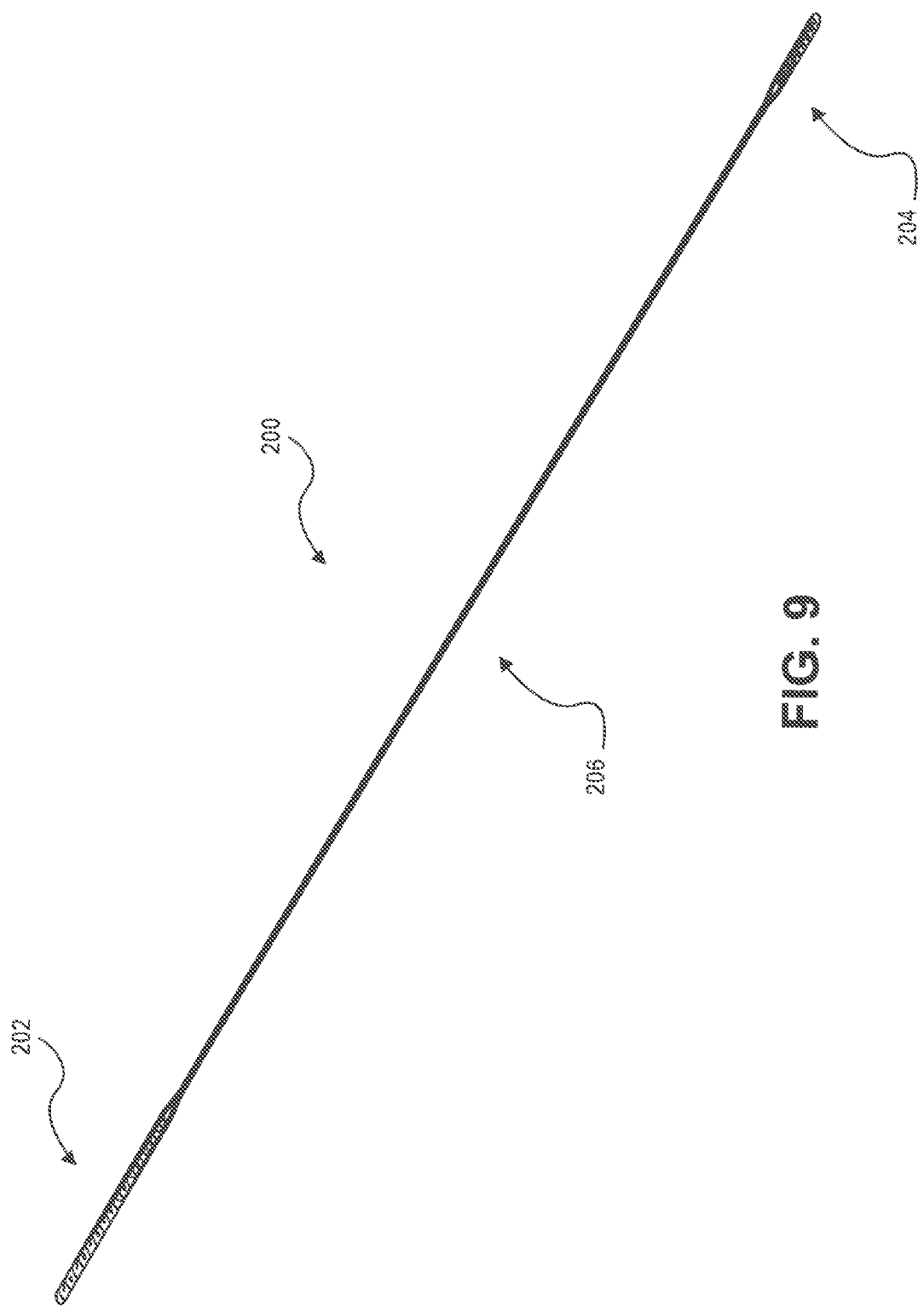
FIG. 9 is an isometric view of the thin film lead of FIG. 8 shown assembled.
Figure 10:
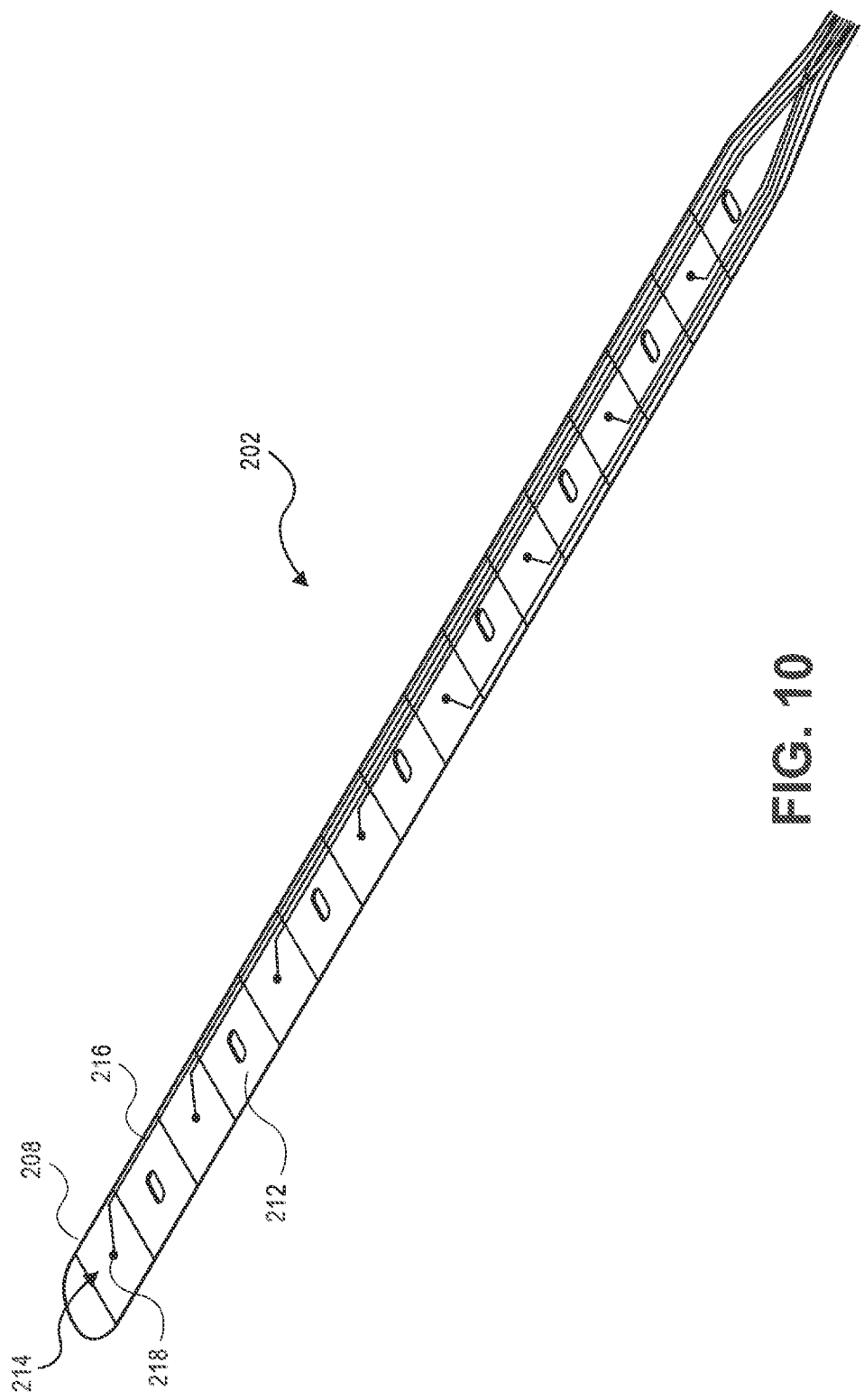
FIG. 10 is a detailed view of a stimulation end of the thin film lead of FIG. 9.
Figure 11:
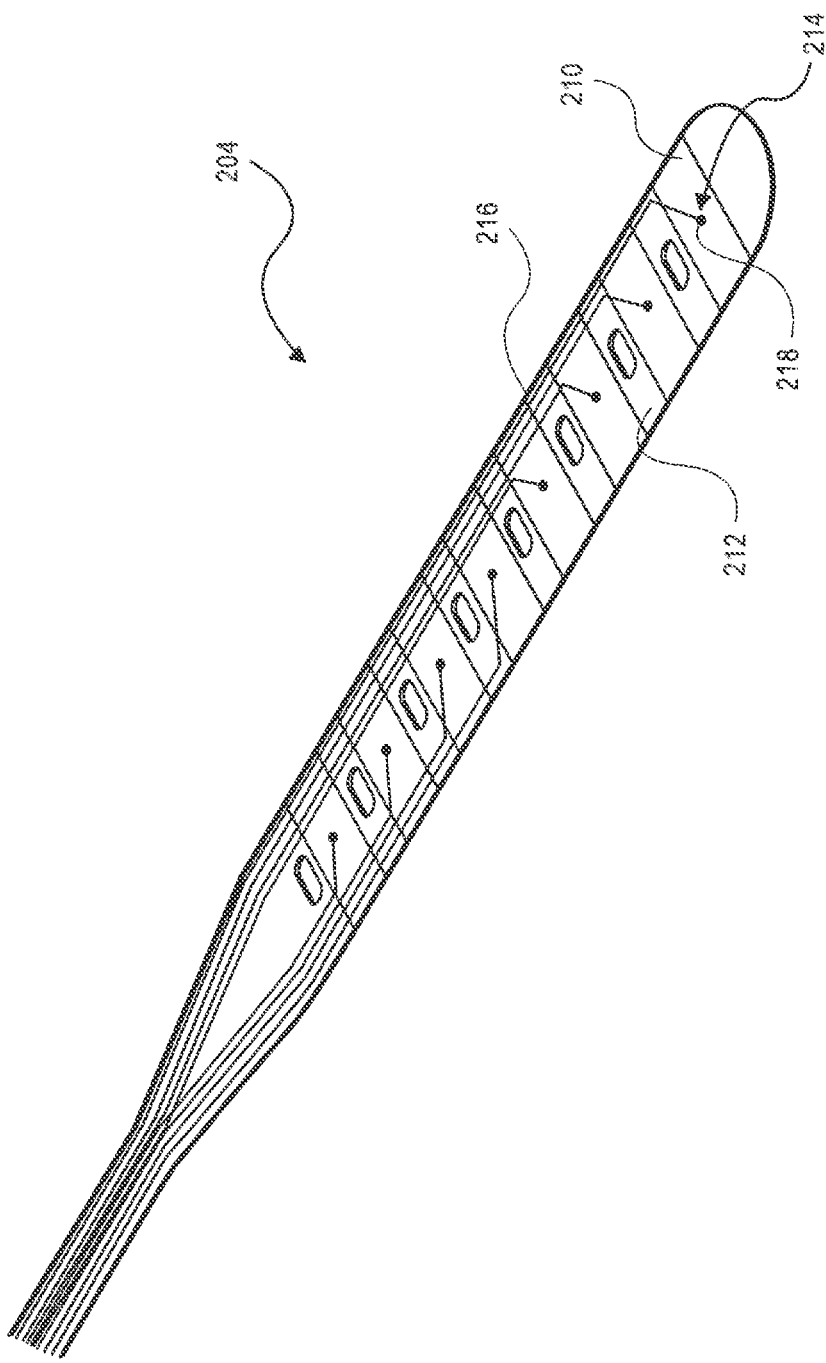
FIG. 11 is a detailed view of a terminal end of the thin film lead of FIG. 9.
Figure 12:
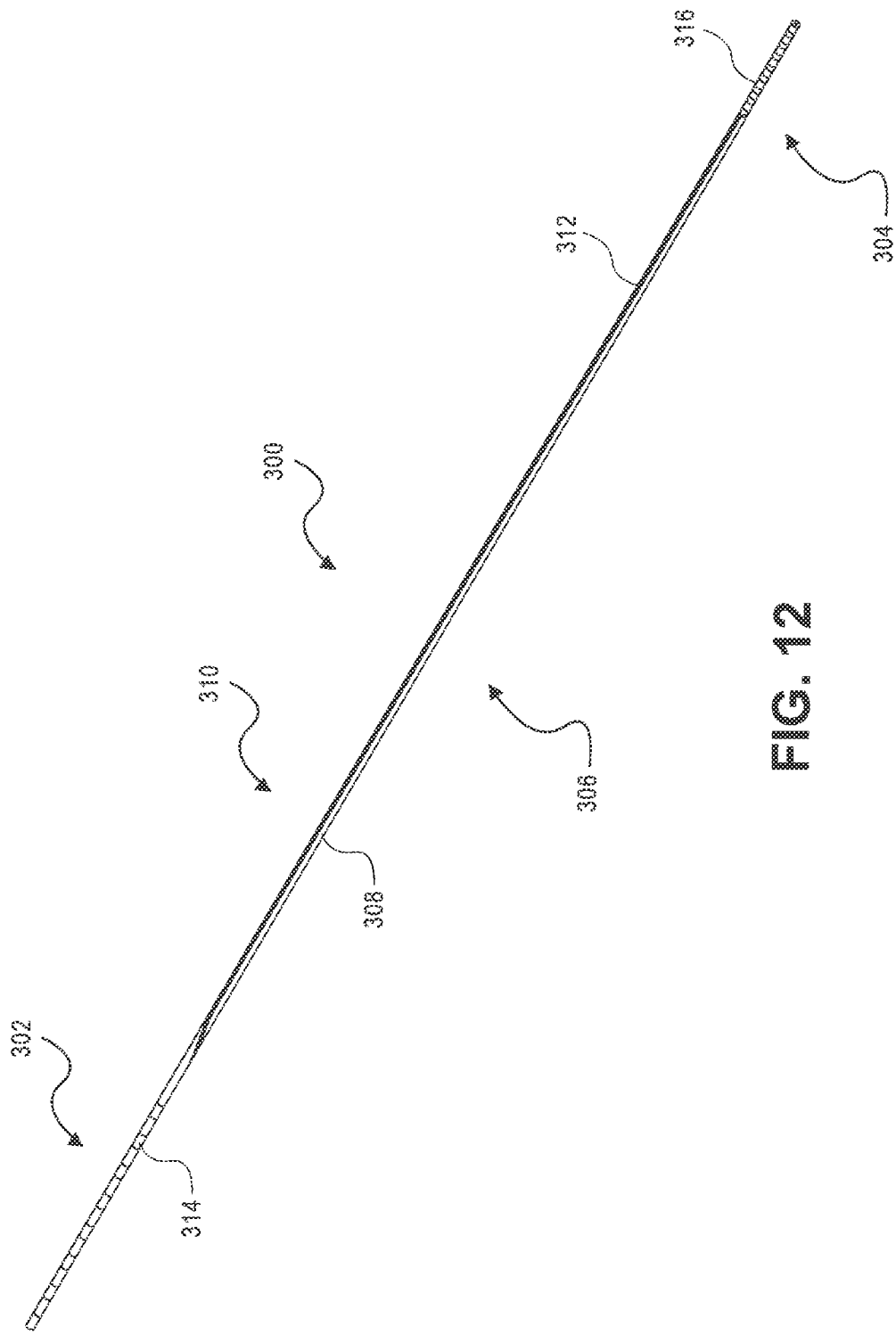
FIG. 12 shows an isometric view of an example cylindrical thin film lead, such as the thin film lead of FIG. 9, wrapped radially around a biocompatible body.
Figure 13:
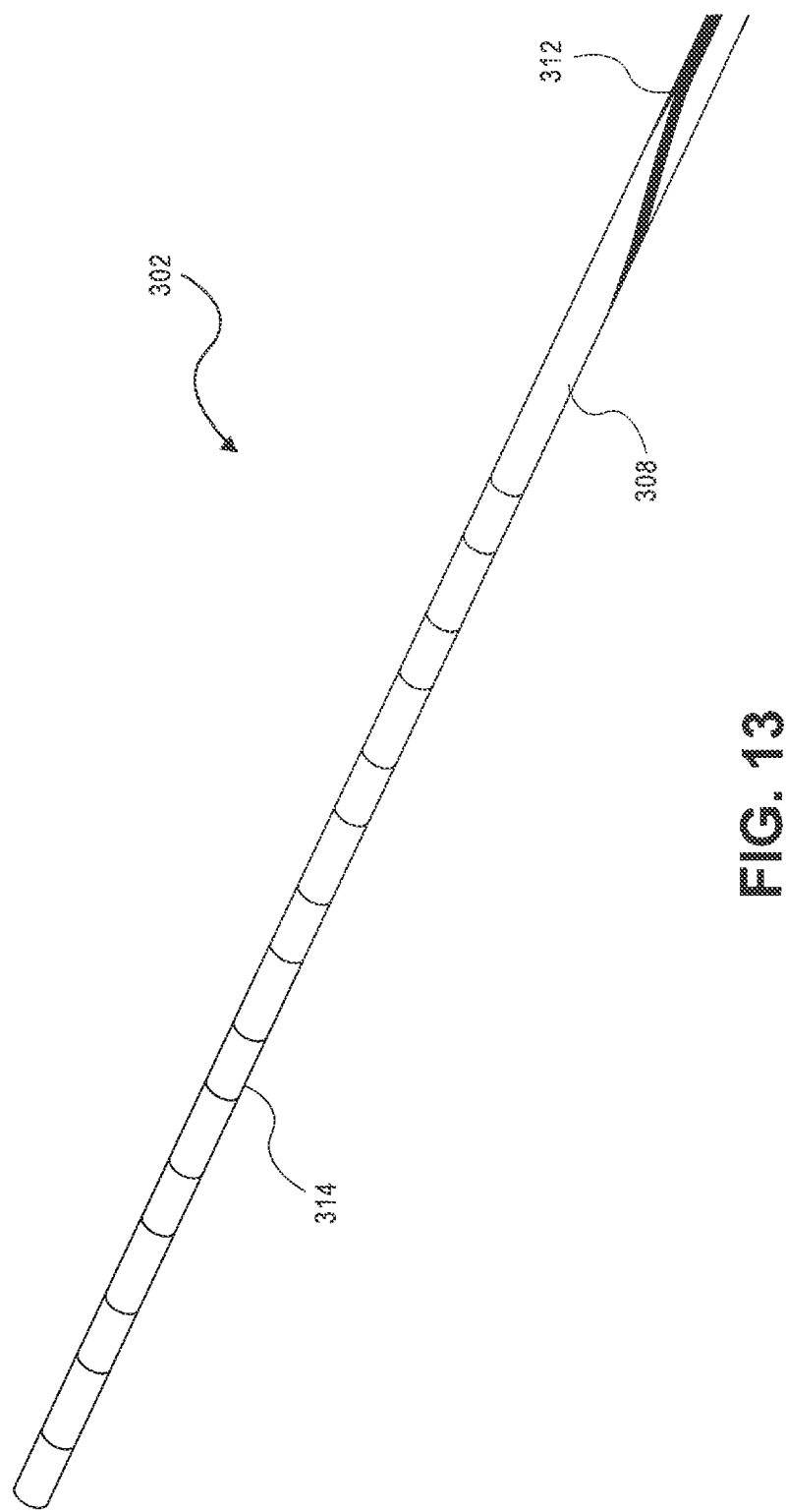
FIG. 13 is a detailed view of a stimulation end of the thin film lead of FIG. 12.
Figure 14:
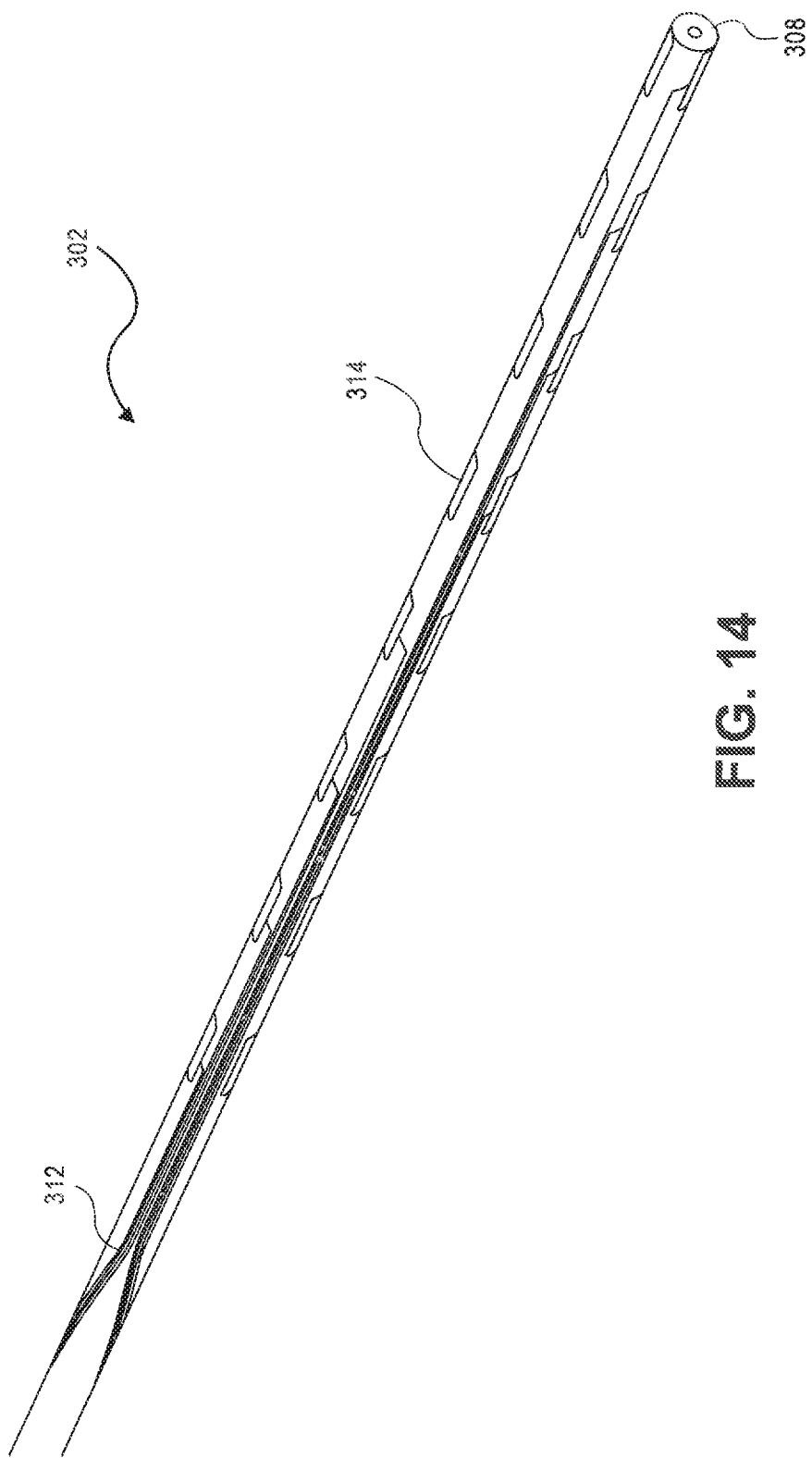
FIG. 14 is another detailed view of the stimulation end of FIG. 13.
Figure 15:
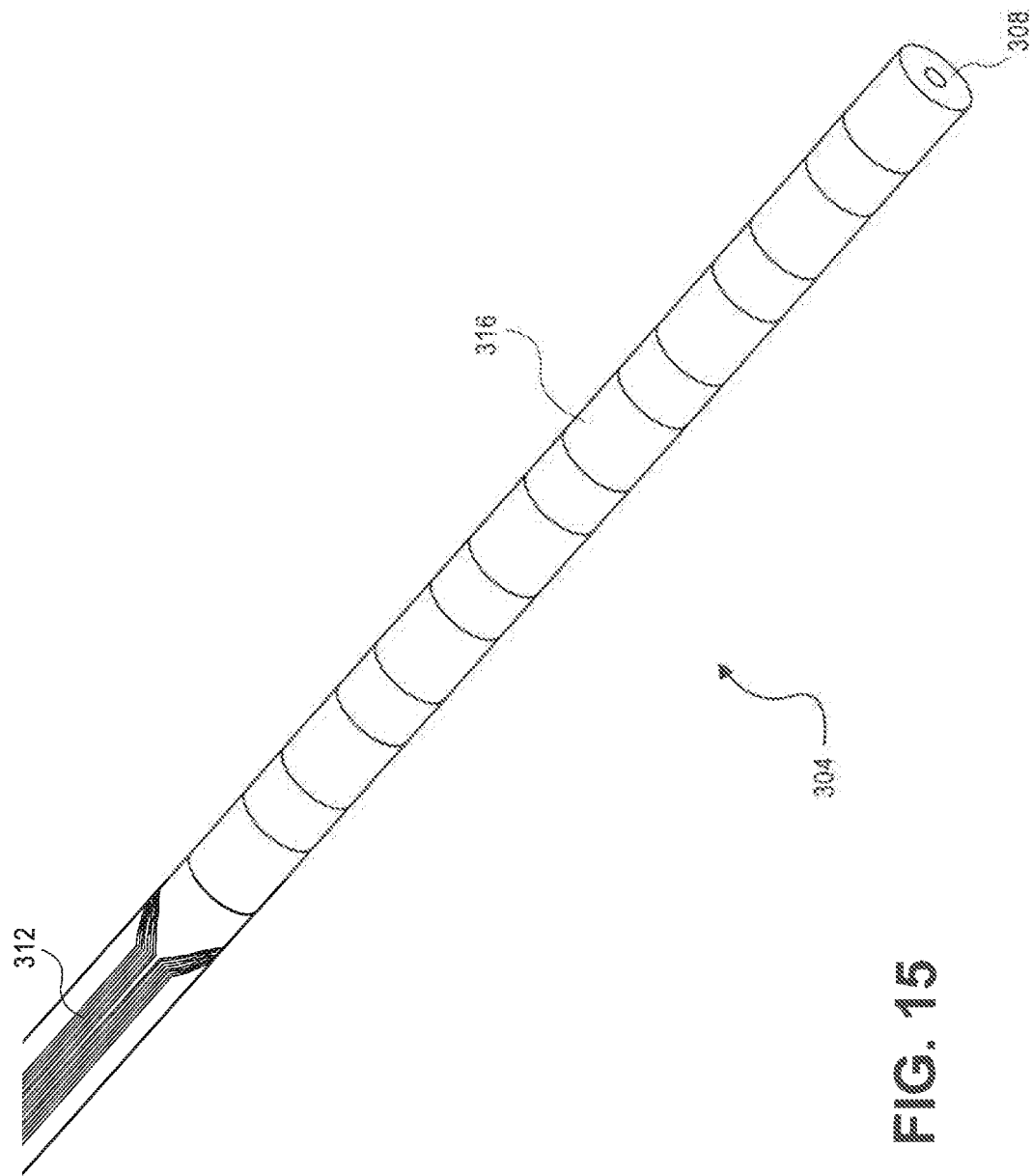
FIG. 15 is a detailed view of a terminal end of the thin film lead of FIG. 12.
Figure 17:
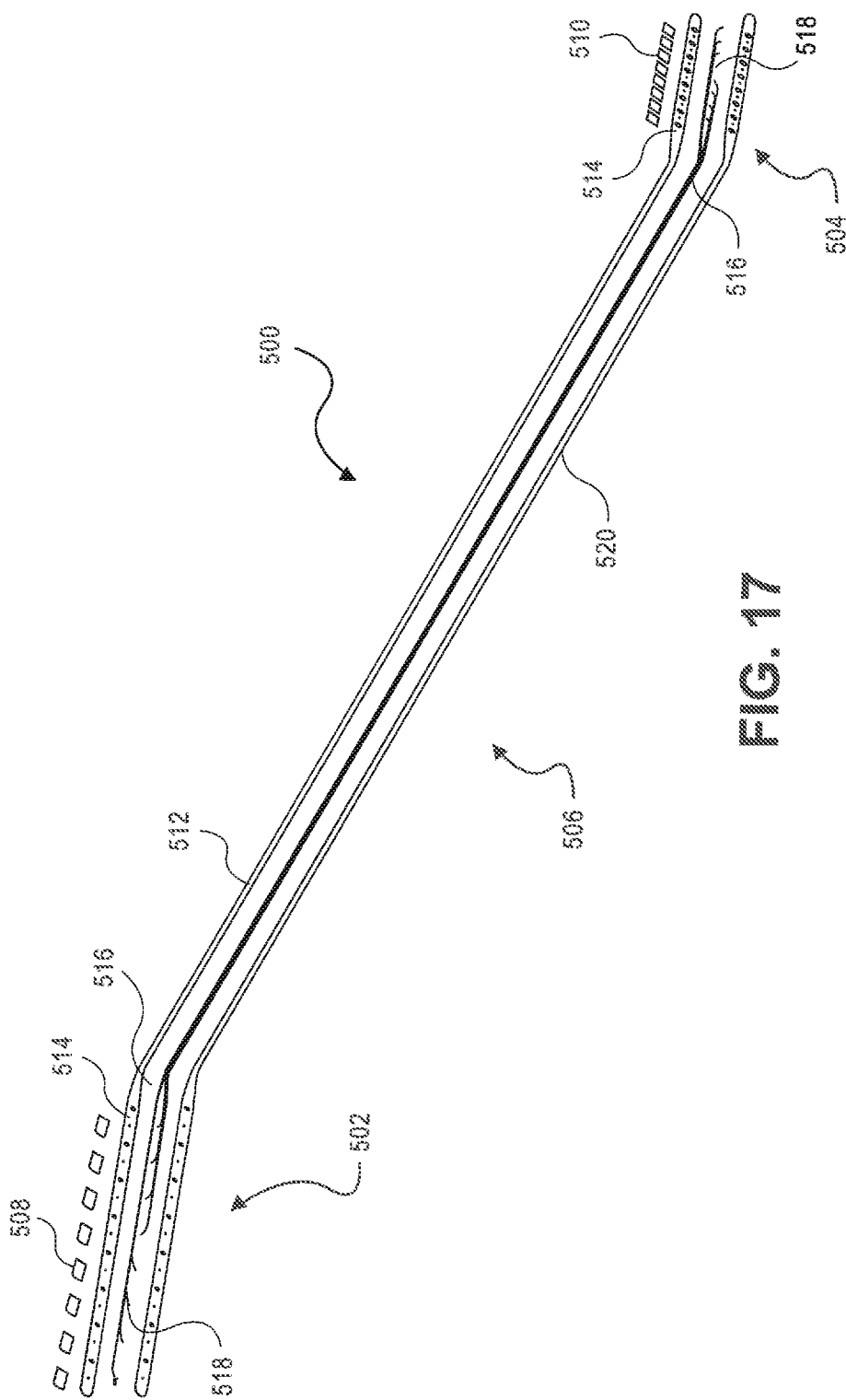
FIG. 17 shows an exploded view of an example thin film tips configured to wrap at a stimulation end and a terminal end and coil at a lead body.
Figure 18:
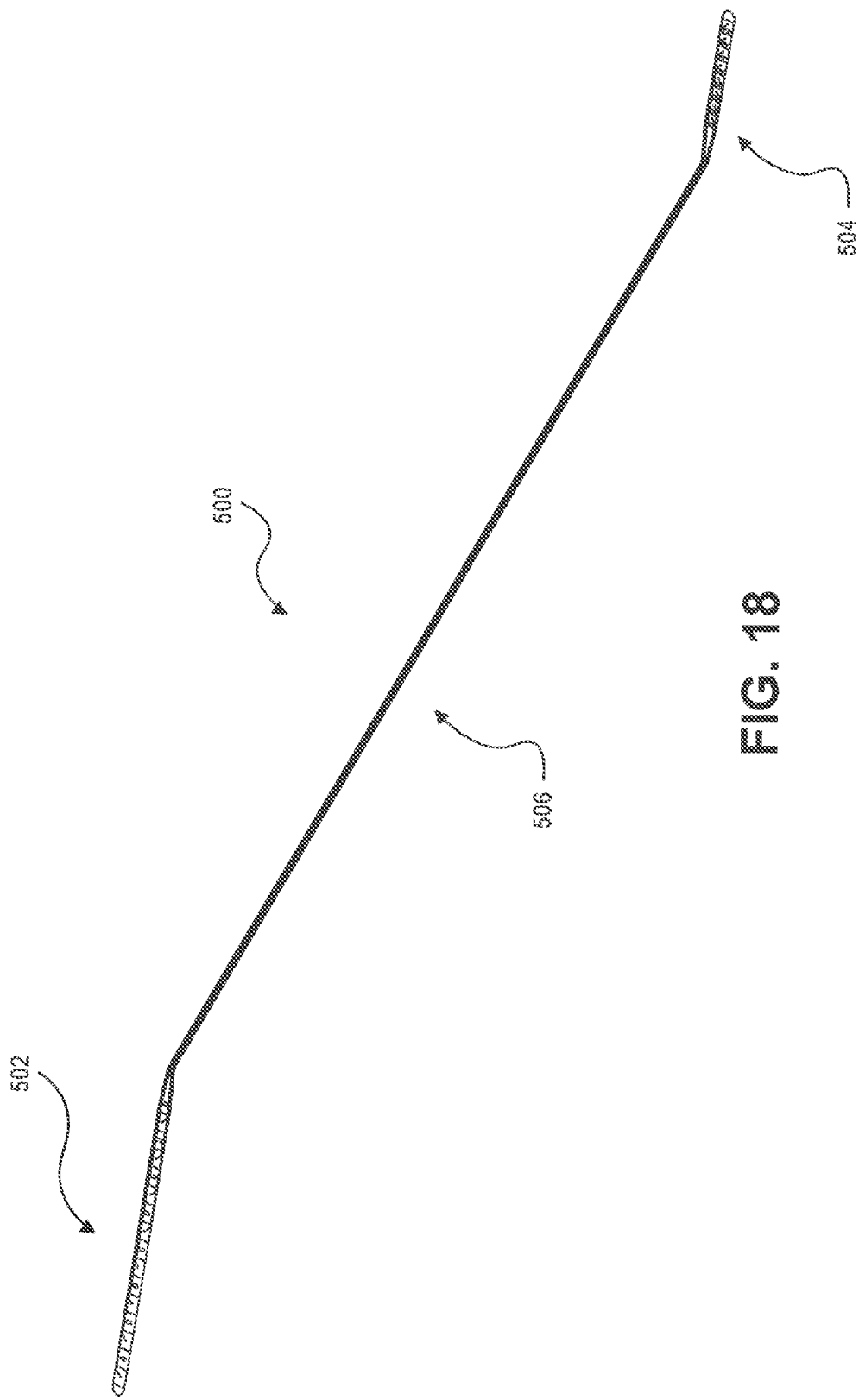
FIG. 18 is an isometric view of the thin film lead of FIG. 17 shown assembled.
Figure 19:
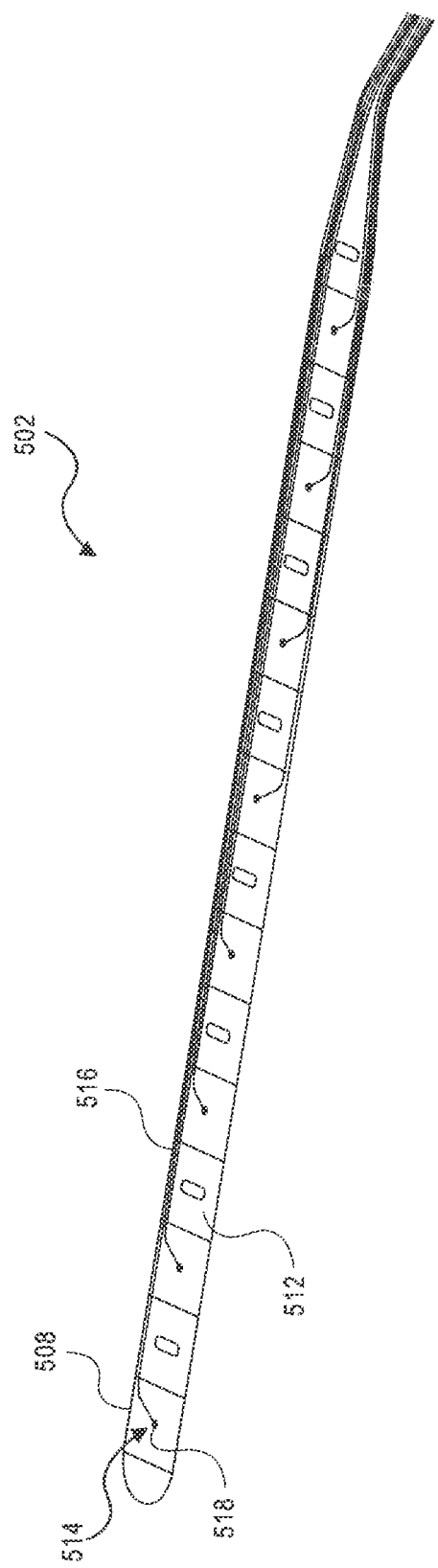
FIG. 19 is a detailed view of a stimulation end of the thin film lead of FIG. 18.
Figure 20:
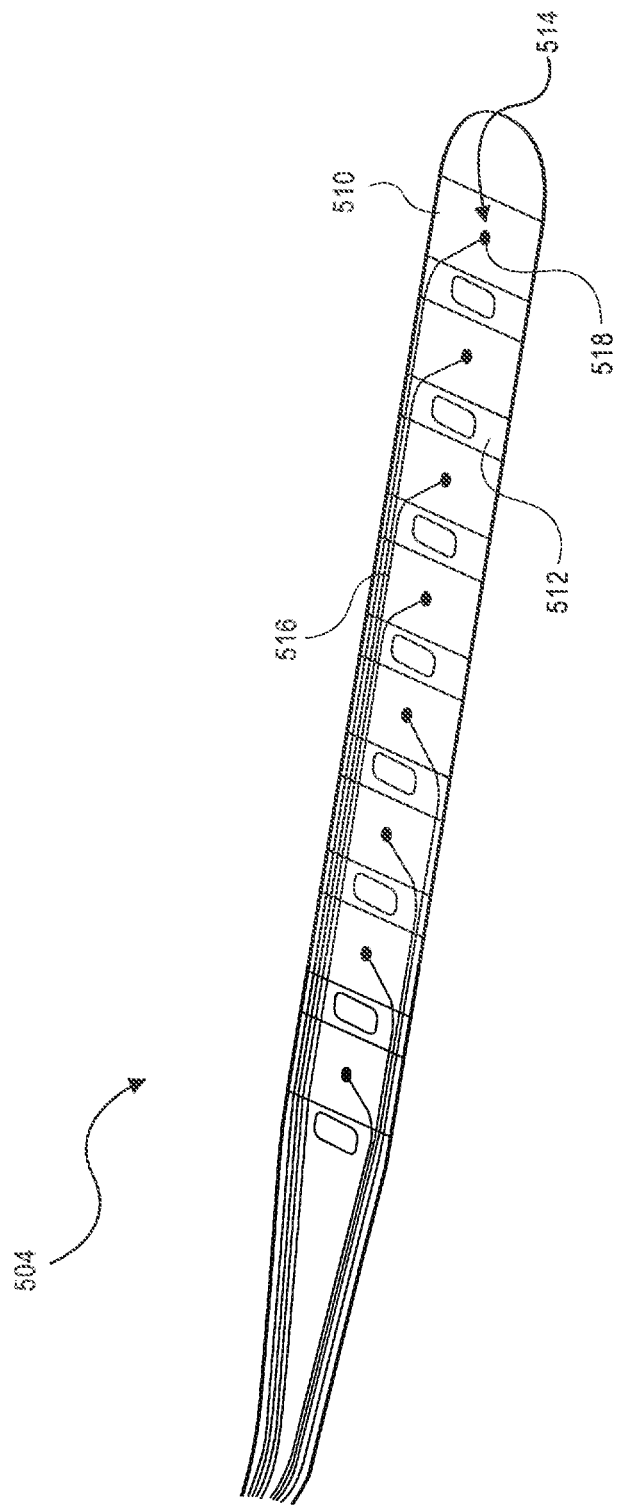
FIG. 20 is a detailed view of a terminal end of the thin film lead of FIG. 18.

Referring to FIGS. 6 and 7, the implantable thin film device 80 is inserted through a lumen of the sheath 114 into the target location of the patient 10 in the epidural space 20. The sheath 114 is then removed, leaving the implantable thin film device 80 in the epidural space 20 to deliver electrical stimulation from the power source 90. The implantable thin film device 80 may be manipulated to achieve a desired SCS therapeutic effect. In one implementation, the implantable thin film device 80 is secured by suturing it to a spinous process (e.g., one of the spinous processes 30).

FIGS. 8-26 depict various examples of the implantable thin film device 80 formed from a flexible circuit, such as a full tip-to-tail flexible circuit, as described herein according to a selected dielectric use. It will be appreciated by those of ordinary skill in the art that such depictions are exemplary only and not intended to be limiting.

Turning first to FIGS. 8-11, the implantable thin film device 80 is formed as a thin film lead 200, which may be wrapped radially around a biocompatible body or mandrel, or deployed flat. In one implementation, the thin film lead 200 is formed from a full tip-to-tail flexible circuit as an eight channel neuromodulation lead for SCS, DBS, or a similar dielectric use.

The thin film lead 200 includes a stimulation end 202 and a terminal end 204 connected by a lead body 206. In one implementation, the stimulation end 202 includes an electrode array 208 having one or more electrodes, and the terminal end 204 includes a connection array 210 having one or more connection spots. As shown in FIGS. 8-11, where the thin film lead 200 is formed from a full tip-to-tail flexible circuit as an eight channel neuromodulation lead, the electrode array 208 and the connection array 210 have eight electrodes and eight connection spots, respectively. In one implementation, the electrodes of the electrode array 208 have a larger surface area relative to the connection spots of the connection array 210, as well as a larger distance between adjacent electrodes of the electrode array 208 relative to a distance between adjacent connection spots of the connection array 210. The relatively larger size and separation distance of the electrode array 208 provides a larger surface area for electrical stimulation delivery in the target location. On the other hand, a decreased size and separation distance of the connection array 210 is beneficial to reduce the footprint of the terminal end 210 and for connection with the power source 90.

In one implementation, the thin film lead 200 includes a shaped insulator 212, which may be formed from a variety of insulating materials, as described herein. In one implementation, the shaped insulator 212 is made from an LCP. The shaped insulator 212 is formed with a profile shaped for SCS, DSB, or a similar dielectric use. For example, as shown in FIGS. 8-11, the shaped insulator 212 may be two-dimensional with a flat profile. Further, the shaped insulator 212 may have a varying shape along the length. For example, the stimulator end 202 and the terminal end 204 of the shaped insulator 212 may each have a larger surface area relative to the lead body 206 of the shaped insulator 212. As shown in FIGS. 8-11, the stimulation end 202 and the terminal end 204 of the shaped insulator 212 may each be shaped like a paddle tapering into the lead body 206. The stimulation end 202 of the shaped insulator 212 may have a larger surface area relative to a surface area of the terminal end 204, based on a surface area of the electrode array 208 and the connection array 210, respectively.

The shaped insulator 212 has an inner surface and an outer surface. In the example shown in FIGS. 8-11, the electrode array 208 and the connection array 210 are fabricated on the outer surface of the shaped insulator 212, and a layer of conductive traces 216 is fabricated on the inner surface of the shaped insulator 212. In one implementation, an insulating layer 220 is applied over the layer of conductive traces 216. The insulating layer 220 may be, for example, an adhesive, such as a low Tg LCP. Although the thin film lead 200 shows one layer of conductive traces and one insulating layer, it will be appreciated that these layers may be part of a multiple-layer series of alternating insulating and conductive layers, as described herein.

In one implementation, one or more vias 214 are formed in the shaped insulator 212 and/or the insulating layer 220 and filled with conductive material 218 to connect the layer of conductive traces 216 to the electrode array 208 and the connection array 210, thereby forming a flexible circuit. A trace pattern is defined by the layer of conductive traces 216 at the stimulation end 202, and a trace pattern is defined by the layer of conductive traces 216 at the terminal end 204 to accommodate the electrode array 208 and the connection array 210 according to the selected dielectric use. In the example shown in FIGS. 8-11, the trace pattern defined by the layer of conductive traces 216 at the stimulation end 202 includes eight traces spaced and shaped such that each of the traces will electrically connect a corresponding electrode in the electrode array 208 with the power source 90. Similarly, the trace pattern defined by the layer of conductive traces 216 at the terminal end 204 includes eight traces spaced and shaped such that each of the traces will electrically connect a corresponding connection spot in the connection array 210 with the lead body 206.

The thin film lead 200 is formed from the flexible circuit according to the selected dielectric use, in the example shown in FIGS. 8-11, SCS, DBS, or the like. In one implementation, the thin film lead 200 is formed directly from the flexible circuit, such that the thin film lead 200 is deployed flat, as shown in FIGS. 8-11.

Turning to FIGS. 12-15, a cylindrical thin film lead 300 having a lead body 306 extending between a stimulation end 302 and a terminal end 304 may be similarly formed from a flexible circuit 310. As described herein, the flexible circuit 310 includes an electrode array 314 disposed at the stimulation end 302 and electrically connected to a connection array 316 disposed at the terminal end 304 by a layer of conductive traces 312. In one implementation, the cylindrical thin film lead 300 is formed from the flexible circuit 310 by radially wrapping the flexible circuit 310 around a biocompatible body 308. Additional views of an example stimulation end 400 of a flexible circuit 402 wrapped around a biocompatible body 404 are shown in FIGS. 16A-16C, with the electrode array 406 disposed on an outer insulating surface 408, such as an outer surface of a shaped insulator or an outer surface of an insulating layer, as described herein.

As shown in FIGS. 17-20, in one implementation, the implantable thin film device 80 is formed as a thin film lead 500, which is wrapped at a stimulation end 502 and a terminal end 504 and coiled at a lead body 506. In one implementation, the thin film lead 500 is formed from a full tip-to-tail flexible circuit as an eight channel neuromodulation lead for SCS, DBS, or a similar dielectric use. The stimulation end 502 is oriented at a first angle to the lead body 506, and the terminal end 504 is oriented at a second angle to the lead body 506, thereby providing increased durability of the thin film lead 500 during movement.

In one implementation, the stimulation end 502 includes an electrode array 508 having one or more electrodes, and the terminal end 504 includes a connection array 510 having one or more connection spots. As shown in FIGS. 17-20, where the thin film lead 500 is formed from a full tip-to-tail flexible circuit as an eight channel neuromodulation lead, the electrode array 508 and the connection array 510 have eight electrodes and eight connection spots, respectively. In one implementation, the electrodes of the electrode array 508 have a larger surface area relative to the connection spots of the connection array 510, as well as a larger distance between adjacent electrodes of the electrode array 508 relative to a distance between adjacent connection spots of the connection array 510. The relatively larger size and separation distance of the electrode array 508 provides a larger surface area for electrical stimulation delivery in the target location. On the other hand, a decreased size and separation distance of the connection array 510 is beneficial to reduce the footprint of the terminal end 510 and for connection with the power source 90.

In one implementation, the thin film lead 500 includes a shaped insulator 512, which may be formed from a variety of insulating materials, as described herein. In one implementation, the shaped insulator 512 is made from an LCP. The shaped insulator 512 is formed with a profile shaped for SCS, DBS, or a similar dielectric use. For example, as shown in FIGS. 17-20, the shaped Insulator 512 may be two-dimensional with a flat profile configured for coiling around the lead body 506. Further, the shaped insulator 512 may have a varying shape along the length. For example, the stimulator end 502 and the terminal end 504 of the shaped insulator 512 may each have a larger surface area relative to the lead body 506 of the shaped insulator 512. As shown in FIGS. 7-20, the stimulation end 502 and the terminal end 504 of the shaped insulator 512 may each be shaped like a paddle tapering into the lead body 506 for coiling into a spiral or helix. The stimulation end 502 of the shaped insulator 512 may have a larger surface area relative to a surface area of the terminal end 504, based on a surface area of the electrode array 508 and the connection array 510, respectively.

The shaped insulator 512 has an inner surface and an outer surface. In the example shown in FIGS. 17-20, the electrode array 508 and the connection array 510 are fabricated on the outer surface of the shaped insulator 512, and a layer of conductive traces 516 is fabricated on the inner surface of the shaped insulator 512. In one implementation, an insulating layer 520 is applied over the layer of conductive traces 516. The insulating layer 520 may be, for example, an adhesive, such as a low Tg LCP. Although the thin film lead 500 shows one layer of conductive traces and one insulating layer, it will be appreciated that these layers may be part of a multiple-layer series of alternating Insulating and conductive layers, as described herein.

In one implementation, one or more vias 514 are formed in the shaped insulator 512 and/or the insulating layer 520 and filled with conductive material 518 to connect the layer of conductive traces 516 to the electrode array 508 and the connection array 510, thereby forming a flexible circuit. A trace pattern is defined by the layer of conductive traces 516 at the stimulation end 502, and a trace pattern is defined by the layer of conductive traces 516 at the terminal end 504 to accommodate the electrode array 508 and the connection array 510 according to the selected dielectric use. In the example shown in FIGS. 17-20, the trace pattern defined by the layer of conductive traces 516 at the stimulation end 502 includes eight traces spaced and shaped such that each of the traces will electrically connect a corresponding electrode in the electrode array 508 with the power source 90. Similarly, the trace pattern defined by the layer of conductive traces 516 at the terminal end 504 includes eight traces spaced and shaped such that each of the traces will electrically connect a corresponding connection spot in the connection array 510 with the lead body 506.

The thin film lead 500 is formed from the flexible circuit according to the selected dielectric use, in the example shown in FIGS. 17-20, SCS, DBS, or the like. In one implementation, the thin film lead 500 is formed by wrapping the flexible circuit at the stimulation end 502 and the terminal end 504 and coiling the flexible circuit at the lead body 506.

Figure 21:
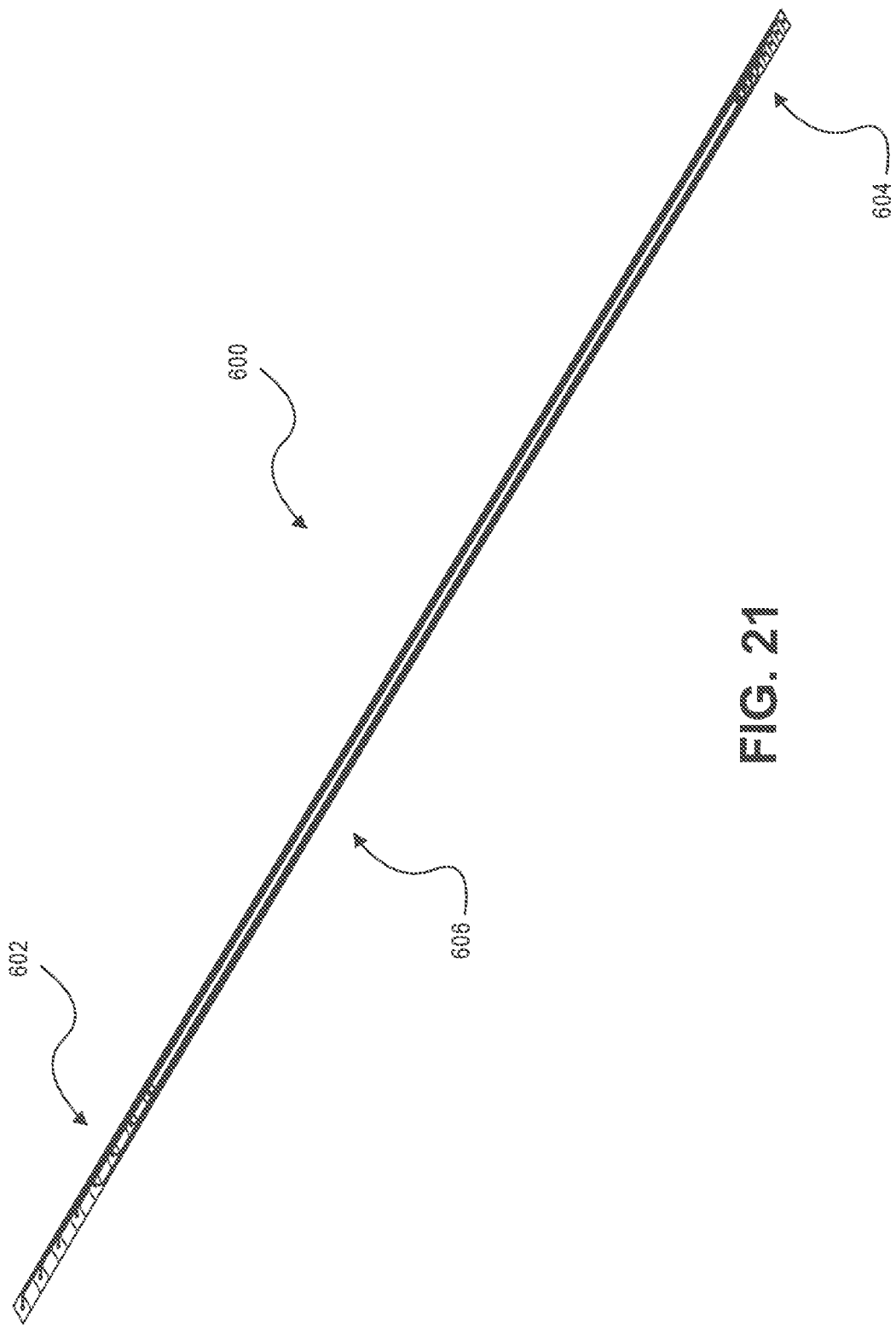
FIG. 21 shows an isometric view of an example thin film paddle lead configured for percutaneous insertion.
Figure 22:
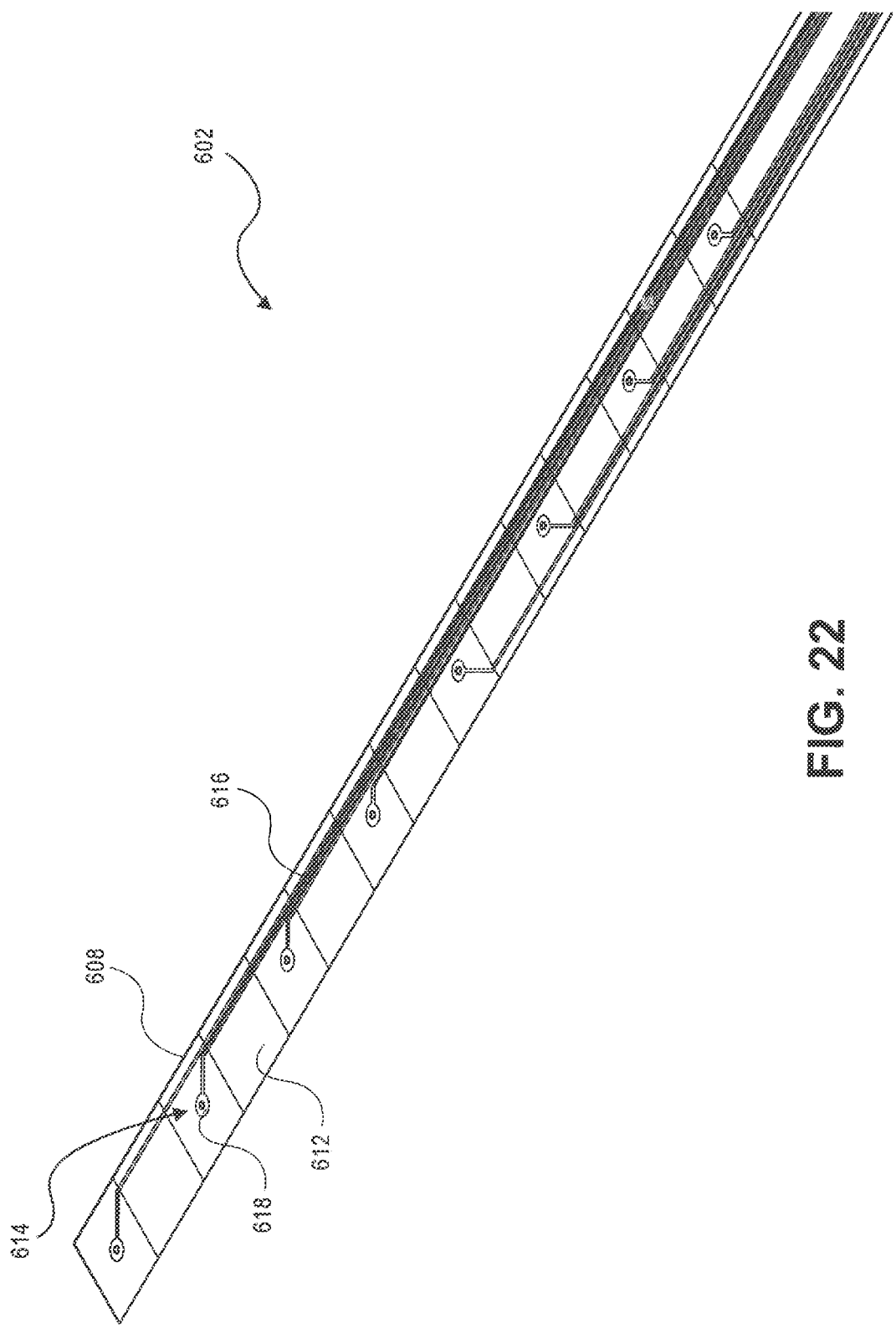
FIG. 22 is a detailed view of a stimulation end of the thin film paddle lead of FIG. 21.
Figure 23:
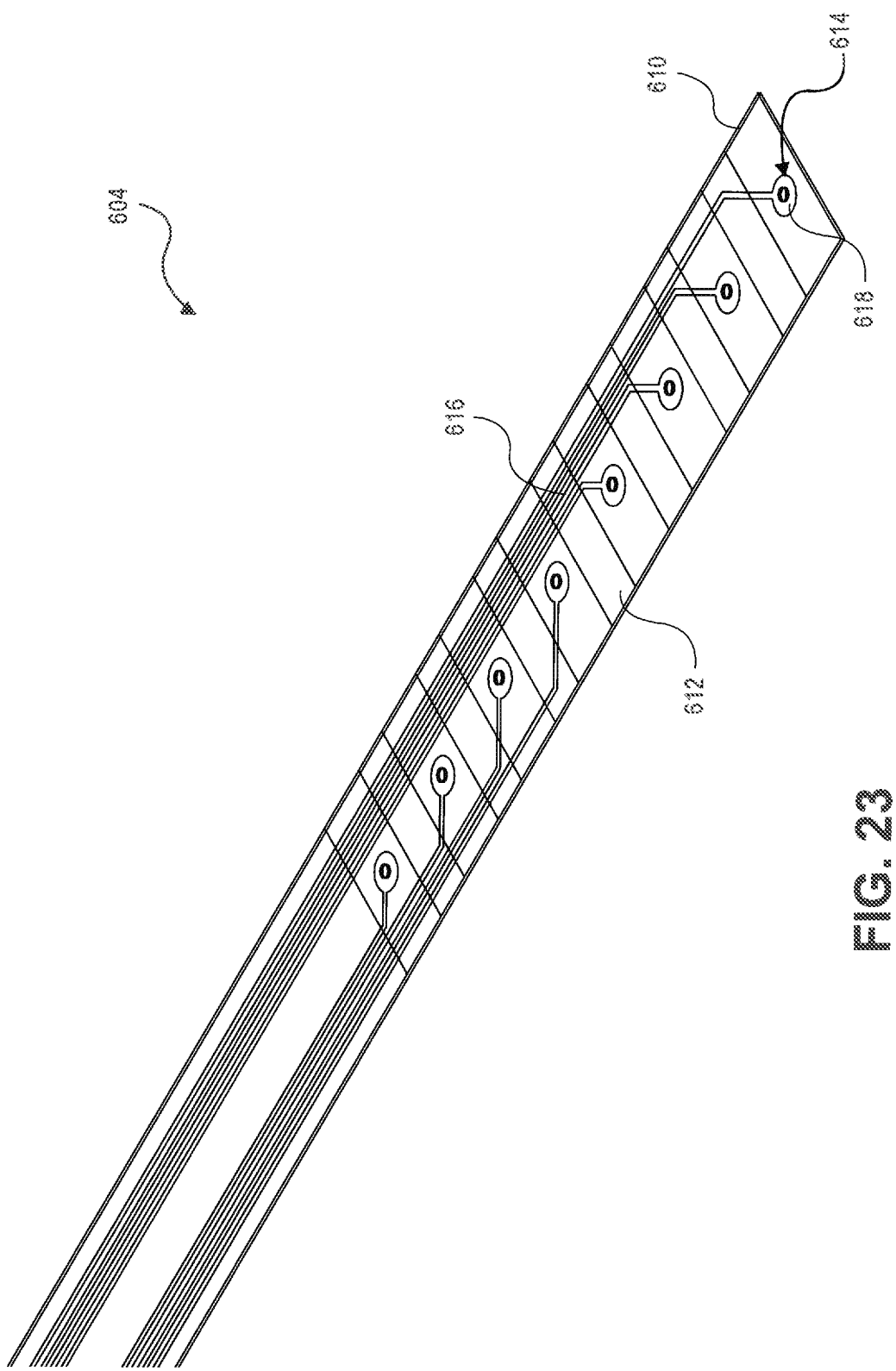
FIG. 23 is a detailed view of a terminal end of the thin film paddle lead of FIG. 21.

Referring to FIGS. 21-23, an example thin film paddle lead 600 configured for percutaneous insertion is depicted. In one implementation, the thin film paddle lead 600 includes a lead body 608 extending between a stimulation end 602 and a terminal end 604. In the example shown in FIGS. 21-23, the thin film paddle lead 600 is formed from a full tip-to-tail flexible circuit as an eight channel neuromodulation lead for SCS, DBS, or a similar dielectric use. The thin film paddle lead 600 is flat and narrow, permitting percutaneous deployment.

In one implementation, the stimulation end 602 includes an electrode array 608 having one or more electrodes, and the terminal end 604 includes a connection array 610 having one or more connection spots. As shown in FIGS. 21-23, where the thin film paddle lead 600 is formed from a full tip-to-tail flexible circuit as an eight channel neuromodulation lead, the electrode array 608 and the connection array 610 have eight electrodes and eight connection spots, respectively. In one implementation, the electrodes of the electrode array 608 have a larger surface area relative to the connection spots of the connection array 610, as well as a larger distance between adjacent electrodes of the electrode array 608 relative to a distance between adjacent connection spots of the connection array 610. The relatively larger size and separation distance of the electrode array 608 provides a larger surface area for electrical stimulation delivery in the target location. On the other hand, a decreased size and separation distance of the connection array 610 is beneficial to reduce the footprint of the terminal end 610 and for connection with the power source 90.

In one implementation, the thin film paddle lead 600 includes a shaped insulator 612, which may be formed from a variety of insulating materials, as described herein. The shaped insulator 612 is formed with a profile shaped for SCS, DBS, or a similar dielectric use. For example, as shown in FIGS. 21-23, the shaped insulator 612 may be two-dimensional with a flat, narrow profile extending along an entirety of a length of the shaped insulator 612. In one implementation, the thin film paddle lead 600 includes an insulating layer formed over a layer of conductive traces 616, which are connected to the electrode array 608 and the connection array 610 using vias 614 filled with conductive material 616, as described herein to form the flexible circuit.

The thin film paddle lead 600 is formed from the flexible circuit according to the selected dielectric use, in the example shown in FIGS. 21-23, SCS, DBS, or the like. In one implementation, the thin film paddle lead 600 is formed directly from the flexible circuit, such that the thin film paddle lead 600 is deployed flat, as shown in FIGS. 21-23, for percutaneous insertion.

Figure 24:
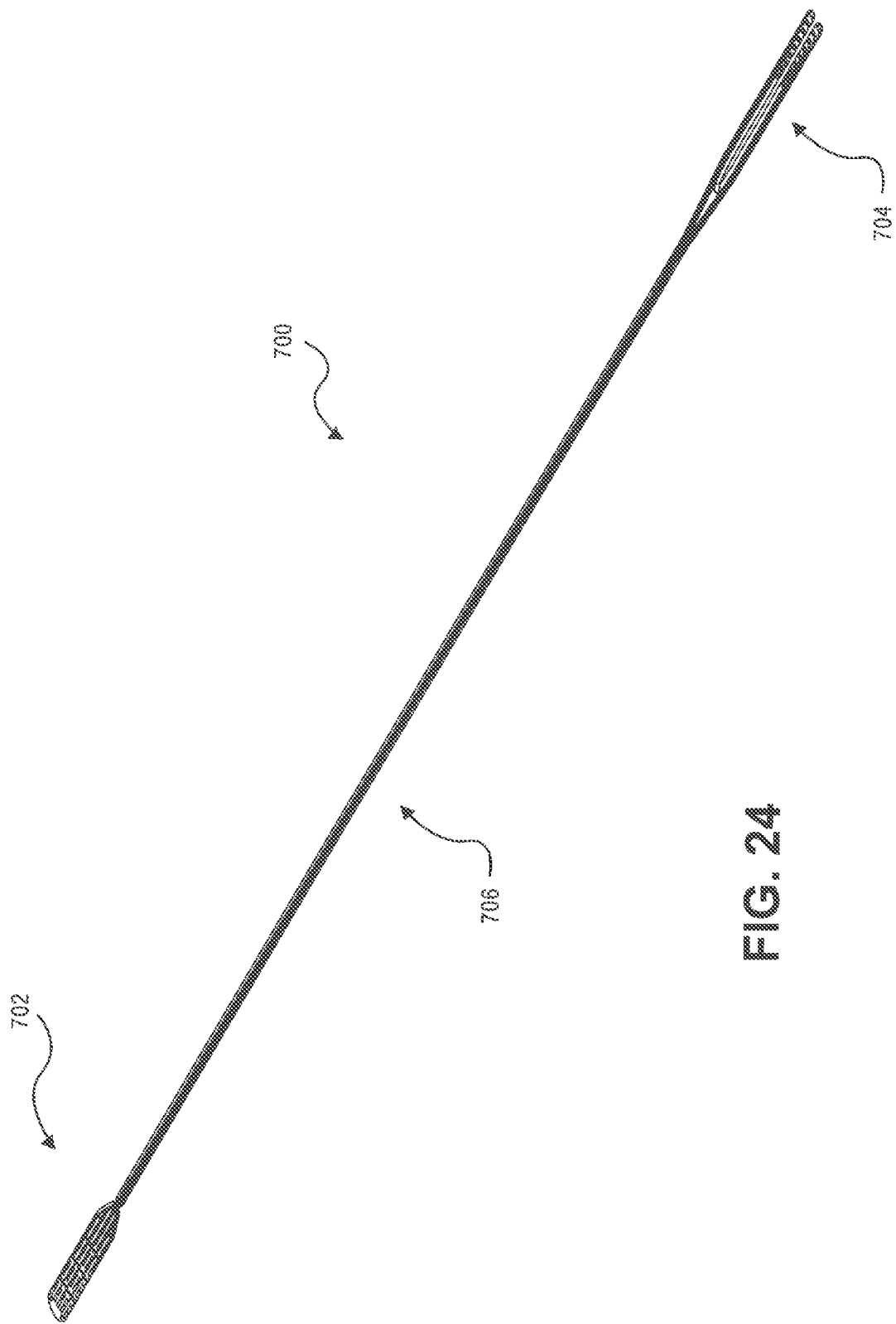
FIG. 24 shows an isometric view of an example thin film paddle lead with a bifurcated terminal end.
Figure 25:
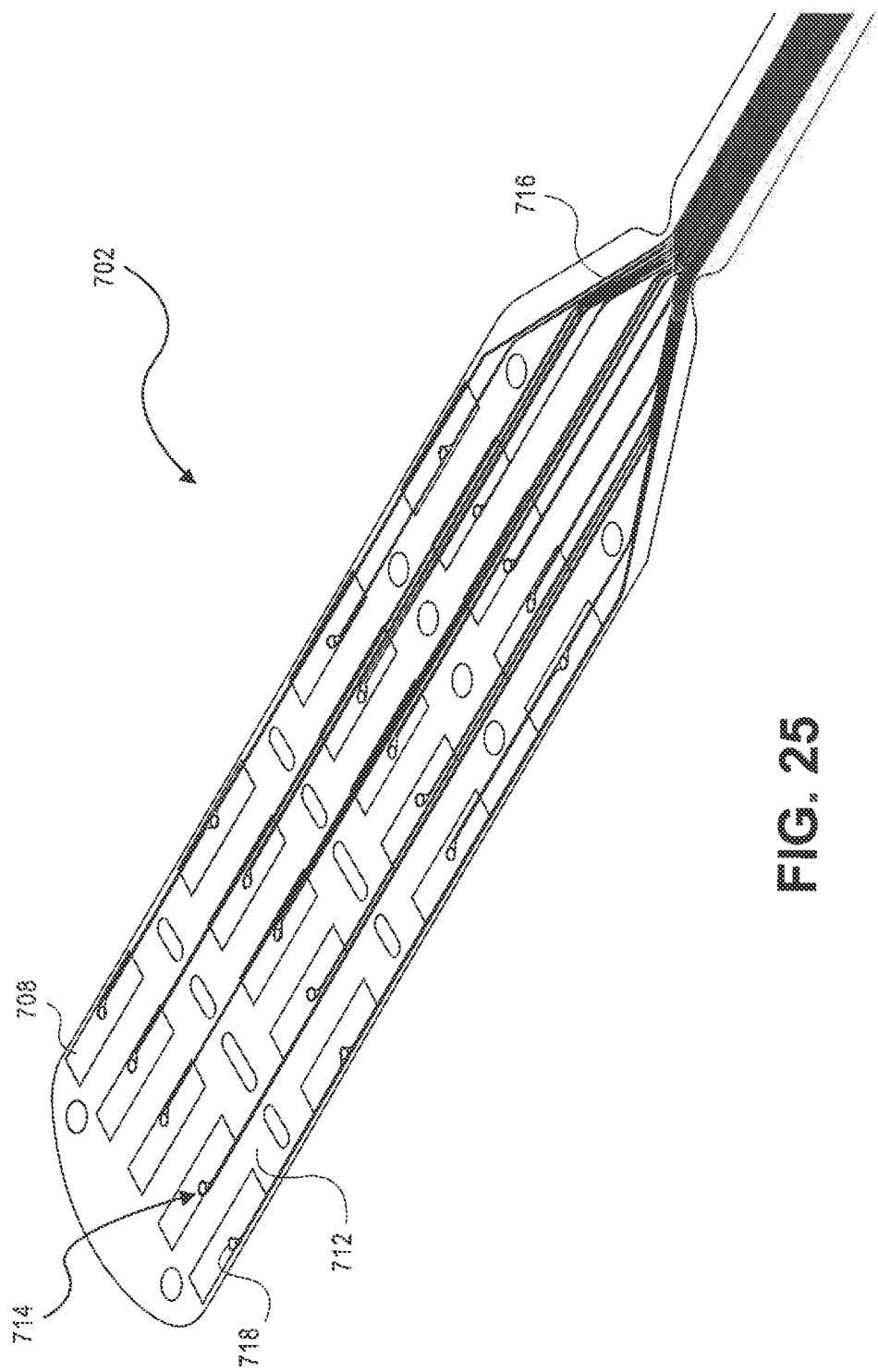
FIG. 25 is a detailed view of a stimulation end of the thin film paddle lead of FIG. 24.
Figure 26:
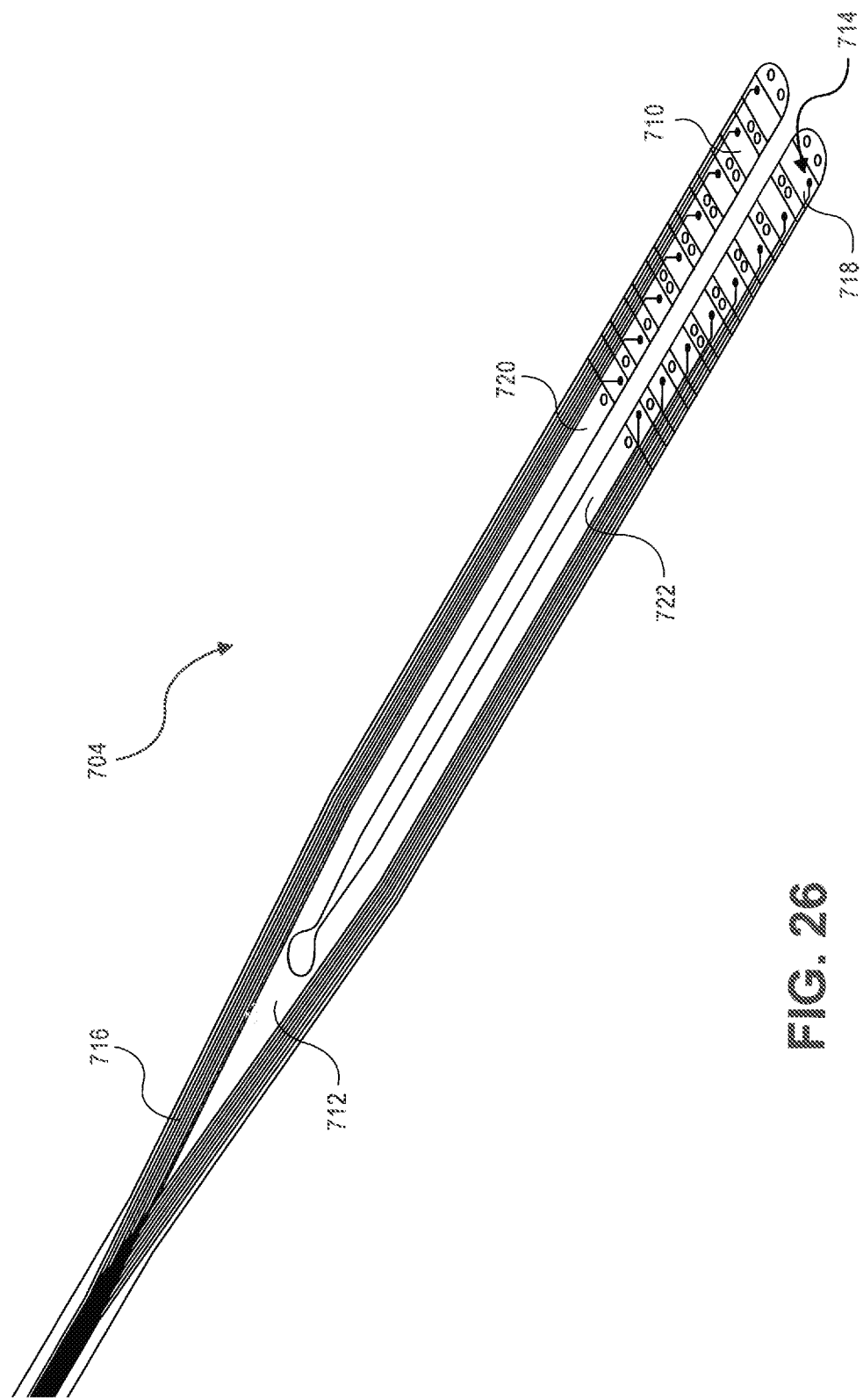
FIG. 26 is a detailed view of the bifurcated terminal end of the thin film paddle lead of FIG. 24.

FIGS. 24-26 show an example thin film paddle lead 700 with a bifurcated terminal end. In one implementation, the thin film paddle lead 700 includes a lead body 706 extending between a stimulation end 702 and a terminal end 704. In the example shown in FIGS. 24-26, the thin film paddle lead 700 is formed from a full tip-to-tail flexible circuit as a multiple-column neuromodulation lead for SCS, DSB, or a similar dielectric use. More particularly, the thin film paddle lead 700 is configured for multiple columns of electrodes (e.g., two eight channel columns) while maintaining a flat, narrow profile to minimize a footprint of the thin film paddle lead 700 and the power source 90.

In one implementation, the stimulation end 702 includes an electrode array 708 having a plurality of columns of electrodes, and the terminal end 704 is bifurcated with a connection array 710 having a plurality of connection spots disposed on a first connection tail 720 and a plurality of connection spots disposed on a second connection tail 722.

In one implementation, the thin film paddle lead 700 includes a shaped insulator 712, which may be formed from a variety of insulating materials, as described herein. The shaped insulator 712 is formed with a profile shaped for SCS, DBS, or a similar dielectric use. For example, as shown in FIGS. 24-26, the shaped insulator 712 may be two-dimensional with a flat, narrow profile. Further, the shaped insulator 712 may have a varying shape along the length. For example, the stimulator end 702 and the terminal end 704 of the shaped insulator 712 may each have a larger surface area relative to the lead body 706 of the shaped insulator 712. As shown in FIGS. 24-26, the stimulation end 702 of the shaped insulator 712 may be shaped like a paddle tapering into the lead body 706. In one implementation, the thin film paddle lead 700 includes an insulating layer formed over a layer of conductive traces 716, which are connected to the electrode array 708 and the connection array 710 using vies 714 filled with conductive material 718, as described herein to form the flexible circuit.

The thin film paddle lead 700 is formed from the flexible circuit according to the selected dielectric use, in the example shown in FIGS. 24-26, SCS, DBS, or the like. In one implementation, the thin film paddle lead 700 is formed directly from the flexible circuit, such that the thin film paddle lead 700 is deployed flat, as shown in FIGS. 24-26.

As can be understood from the present disclosure, a thin film circuit may be formed for a selected dielectric use. Using such thin film circuits, implantable thin film devices may include electrodes and contacts in various customized shapes, sizes, and/or locations on a substrate, which may eliminate the need for mechanical components to fabricate, connect, and attach to a power source. Similarly, the thin film circuits may be formed in a variety of shapes, including, without limitation, circular, spiral, and the like, to aid in delivery and durability. The thin film circuit may be further customized with a desired aspect ratio, width to length, using large format processing, roll to roll processing, stitching multiple circuits together, and/or the like. To minimize the invasiveness to a patient, the footprint of the implantable thin film device is reduced, for example, by shrinking the volume and/or forming the implantable thin film device for flat deployment. The implantable thin film devices may also be formed from a three-dimensional substrate having a shape customized for the selected dielectric use. Conductive channels are formed on the three-dimensional substrate.

These features and advantages provide the ability to deliver and/or sense location specific signals within the body of a patient without complex assemblies having multiple bulky mechanical components being constructed and deployed in for different dielectric uses. Conventional assemblies, for example, utilize individual conductors routed through long narrow substrates to deliver and/or receive signals from a location in the patient to a remote generator and/or analysis tool. The individual conductors of such conventional assemblies typically each require a connection to an electrode or contact at the distal and proximal ends to provide an interface to the patient and the generator and/or analysis tool. With the overall length, size, and number of conductors varying depending on the dielectric use, the assembly process for such conventional assemblies can be daunting. For example, the individual conductors in such conventional assemblies are generally comprised of wire and/or cables that are manually routed through delivery substrates, such as tubes. The individual conductors then need to be correctly spaced and joined to an electrode at the distal end and a contact at the proximal end. Organizing the spacing of the electrodes and contacts, as well as ensuring that the appropriate conductor is joined to the appropriate electrode/contact is thus often tedious and time consuming. Further, the junction methods for the electrodes/contacts can be challenging to fixture and to verify the desired characteristics for delivering and/or receiving signals are consistently achieved. These challenges are further exacerbated when accounting for the additional considerations for a particular dielectric use, including, but not limited to, final dimensions, footprint, flexibility, durability, biocompatibility, and the like.

As described herein, the presently disclosed technology addresses these concerns by utilizing thin film circuits customized according to a selected dielectric use, thereby providing simplified fabrication of otherwise complex implantable devices. The presently discloses technology enables the fabrication of thin, flexible multilayer circuits with a reduced footprint and increased function of the assembly, for example, through the integration of both mechanical and electrical components. For a detailed description of example thin film circuits customized for a selected dielectric use and the manufacturing processes associated therewith, reference is made to FIGS. 27-33.

Turning first to FIG. 27, an example thin film circuit 800 having a layer of conductive traces 804 deployed on a three-dimensional substrate 802 is illustrated. As described herein, the three-dimensional substrate 802 is formed as a shaped insulator with a profile being non-flat, for example, curved, angled, and/or irregular. In one implementation, as shown in FIGS. 28A-B, the three-dimensional substrate 802 is a lube having a curved profile shape. The three-dimensional substrate 802 may be flexible or rigid, depending on the selected dielectric use, and may be made from a variety of materials, such as polyimide, glass, ceramic, and/or other biocompatible insulating materials.

Once the three-dimensional substrate 802 is formed as the shaped insulator, the layer of conductive traces 804 is fabricated on the inner surface of the three-dimensional substrate 802 using biocompatible metallization. The layer of conductive traces defines a trace pattern. In one implementation, the trace pattern includes one or more stimulation end traces, terminal end traces, and body traces.

In one implementation, the biocompatible metallization includes metal deposition, foil attachment (e.g., laminated foils), conductive printing, and/or the like using one or more metals. The trace pattern may be defined using resist printing, laser ablation, etching, conductive printing, and/or the like. For example, the layer of conductive traces may be fabricated using a fully biocompatible deposited or etched foil metal scheme. The metals may include, without limitation, Palladium (Pd), Gold (Au), Titanium (Ti), Platinum (Pt), and/or Platinum-Iridium (Pt—Ir). It will be appreciated, however, that other biocompatible metals or electrically conductive materials may be used.

Once the layer of conductive traces 804 is fabricated on the three-dimensional substrate 802, an insulating layer may be applied to the shaped insulator over the layer of conductive traces. In one implementation, the insulating layer is applied with intimate contact between the inner surface of the shaped surface and an inner surface of the insulating layer outside the trace pattern. Stated differently, after application, there is intimate contact between the inner surface of the shaped insulator and the inner surface of the insulating layer where there are no traces, thereby encapsulating the layer of conductive traces between the shaped insulator and the insulating layer. The insulating layer may be made from an insulating material, including, without limitation, polyimide, organic thermoplastic polymer (e.g., PEEK), LCP, glass, ceramic, and/or other flexible or rigid insulating materials. The insulating layer may be applied through extrusion, coating, casting, deposition, lamination, printing, and/or the like.

In one implementation, once the insulating layer is applied, the layer of conducting traces 804 is encapsulated between the inner layer of the insulating layer and the inner layer of the three-dimensional substrate 802. In another implementation, the insulating layer and the layer of conductive traces are part of a multiple-layer series of alternating insulating and conducting layers. An electrode array having one or more electrodes and a connection array having one or more connection spots are fabricated on an outer surface of the three-dimensional substrate 802 and/or the outer surface of the insulating layer. In one implementation, the electrode array and the connection array are in electrical communication with the layer of conductive traces 804 to form a flexible circuit using vias filled with conductive material, for example.

In one implementation, the three-dimensional substrate 802 uses fiber optics to print the layer of conductive traces 804 directly onto a substrate shaped for a selected dielectric use. For example, the three-dimensional substrate 802 may be shaped as a tube, as shown in FIGS. 28A-28B, to manufactured leads or EP catheter devices without a bimetallic strip and additional mechanical or electrical connections with the power source 90.

For an example of a thin film lead 900 having a three-dimensional substrate 902 deployed in the form of a tube, reference is made to FIGS. 28A and 28B. In one implementation, the thin film lead 900 includes a layer of conductive traces 904 and an electrode array having one or more electrodes 906 in electrical communication with the layer of conductive traces 904 fabricated on the three-dimensional substrate 902.

Referring generally to FIGS. 29A-33, it will be appreciated that the implantable thin film devices are manufactured using materials that prevent the environment of the body at the target location from impacting the functionality of the implantable thin film device or adversely affecting the patient over the term of the therapy. As such, the implantable thin film device is manufactured using a substrate formed from a material adapted to withstand processing conditions involved in the application of conductive arrays and junctions as well as to withstand the biochemistry within a patient body without causing any adverse reactions. These materials may include, without limitation, LCP, PEEK, FR-4, polyimide, polytetrafluoroethylene (PTFE), silicon, flexible glass, and/or other materials having resilience to high temperatures, moisture absorption, dimensional stability, and dielectric strength.

The substrate is bonded to another substrate with a layer of conductive traces disposed therebetween. The substrate layers may be bonded through the addition of an adhesive between the layers, thermal bonding, coating, and/or the like. In one implementation, the substrate layers are formed from LCP, which permits the Glass transition temperature (Tg) of the raw material to be varied, thereby enabling thermal bonding of the substrate layers together without distorting the layer of conductive traces deposited on the substrate with the higher Tg. The substrate may be formed into a film from the LCP through solvent casting, extrusion, and/or the like. Extrusion utilizes a counter rotating die in an extruder head to provide uniform dimensional and physical stability to the substrate.

As described herein, the layer of conductive traces is formed using biocompatible metallization. Selection of the conductive material thus balances the conductive characteristics of the material and the ability to pattern and etch traces in the material with the ability to withstand body chemistry and environment. For example, copper is conventionally utilized in thin film technologies due to its excellent conductive properties and the ability to pattern and etch copper as desired. However, in the context of a long term implant device, copper is prone to degradation, corrosion, leaching, and other problems when exposed to the chemistry and environment of the body. As such, a less reactive conductive material, such as Titanium, Gold, Platinum, or similar materials or alloys, may be used for the layer of conductive traces. The layer of conductive traces comprising one or more of these conductive materials is thus deposited on the substrate where it is patterned and etched, for example, through a plated through hole integration, a sequential metal integration, and/or the like.

Figure 29A:
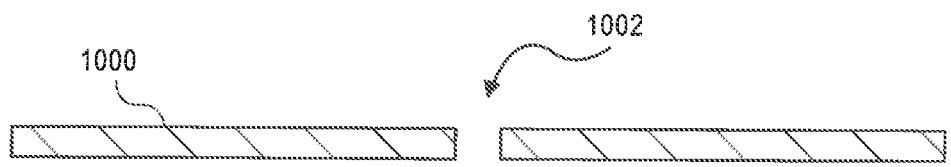
FIGS. 29A-29E show a plated through hole integration process for forming an implantable thin film device.
Figure 29B:
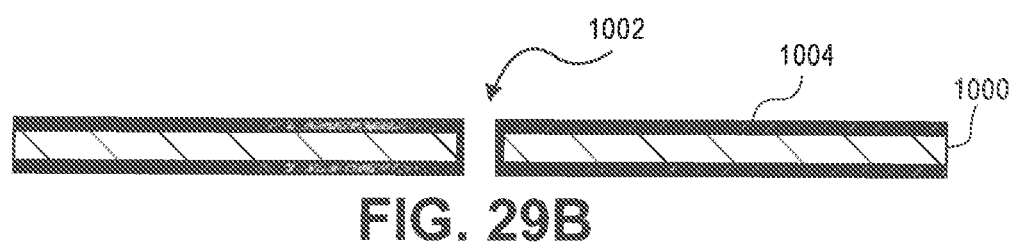
Figure 29C:
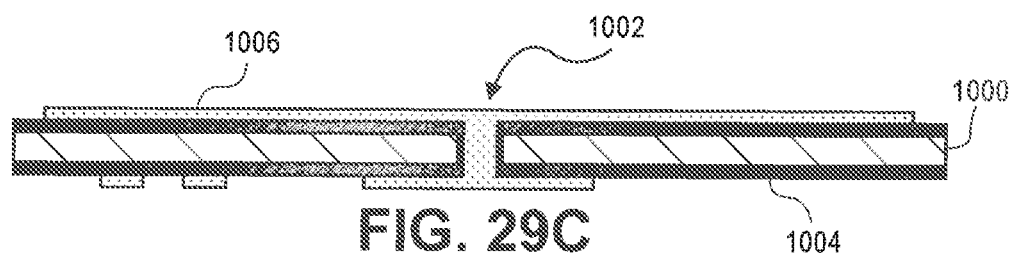
Figure 29D:
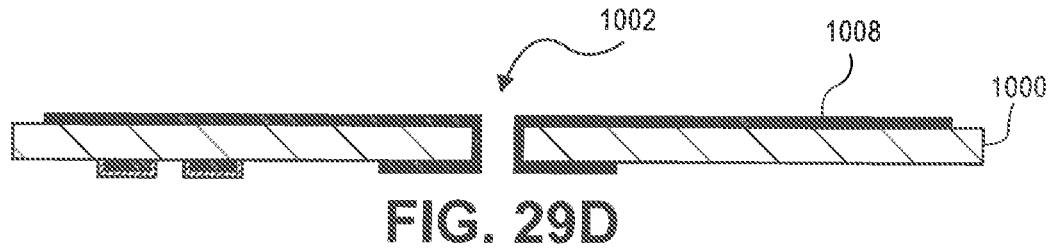
Figure 29E:
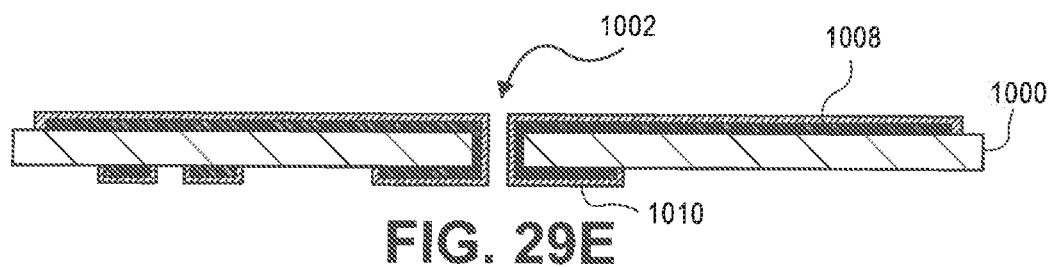

For a detailed description of plated through hole integration, reference is made to FIGS. 29A-29E. In one implementation, a substrate 1000 is formed according to a selected dielectric use, as described herein. One or more vias 1002 are formed in the substrate 1000, as shown in FIG. 29A. In one implementation, the vias are laser drilled. As shown in FIG. 29B, a conductive seed layer 1004 is deposited on one or more surfaces of the substrate 1000. The conductive seed layer 1004 may comprise one or more layers of biocompatible metal. Turning to FIGS. 29C-29D, a trace pattern 1008 is defined in the conductive seed layer 1004. In one implementation, resist 1006 is deposited to pattern the conductive seed layer 1004. The conductive seed layer 1004 is etched and the resist 1006 is removed, thereby forming the trace pattern 1008. As can be understood from FIG. 29E, an electroplate 1010 is deposited on the trace pattern 1008.

Figure 30A:
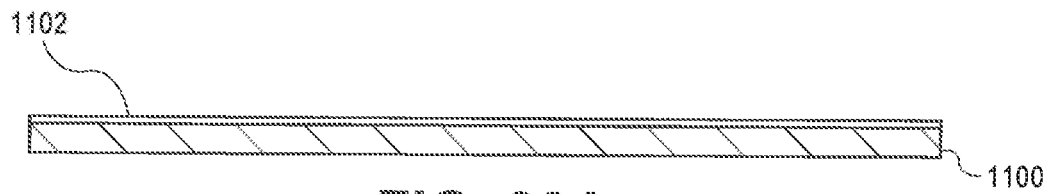
FIGS. 30A-30G depict a sequential metal integration process for forming an implantable thin film device.
Figure 30B:
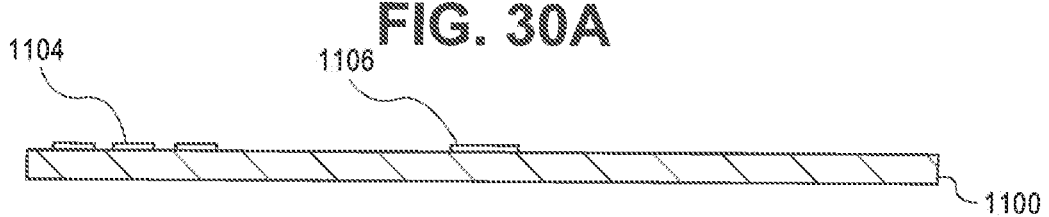
Figure 30C:
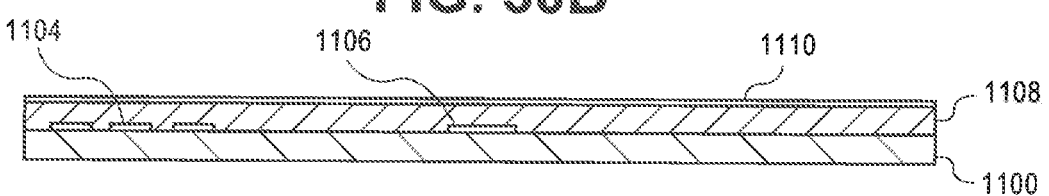
Figure 30D:
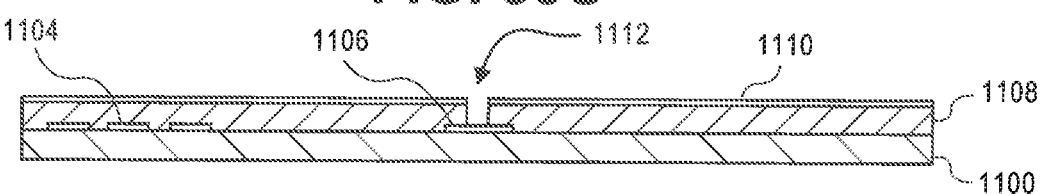
Figure 30E:
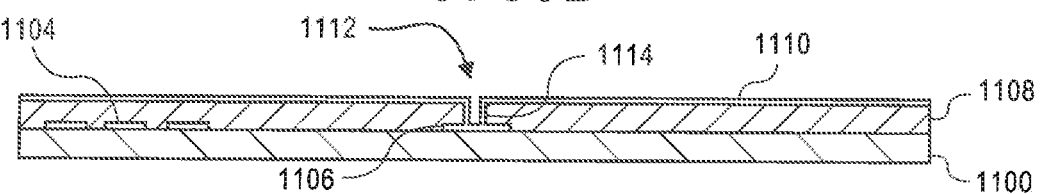
Figure 30F:
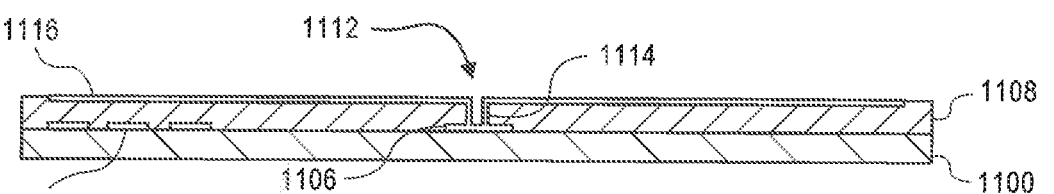
Figure 30G:
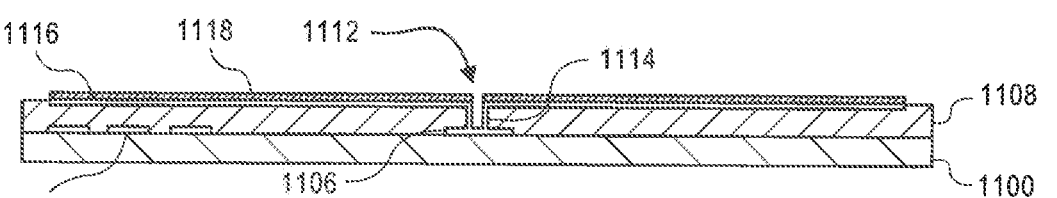

Referring to FIGS. 30A-30G, an example sequential metal integration process is illustrated. Referring first to FIG. 30A, in one implementation, a first substrate 1100 is formed according to a selected dielectric use, as described herein, and a first conductive layer 1102 is deposited on one or more surfaces of the substrate 1100. The first conductive layer 1102 may comprise one or more layers of biocompatible metal. As shown in FIG. 30B, the first conductive layer 1102 is patterned and wet etched to form a trace pattern with one or more conductive interconnects 1104 and 1106. In the alternative, a conductive seed layer, through mask plate, and seed etch may be used. Turning to FIG. 30C, a second substrate 1108 is laminated to the first substrate 1100 over the conductive interconnects 1104 and 1006, and a second conductive layer 1110 is deposited on at least one of an outer surface of the first substrate 1100 or the second substrate 1108. FIG. 30D shows at least one via 1112 formed in the first substrate 1100 or the second substrate 1108 depending on the deposition of the second conductive layer 1110. In one implementation, the via 1112 is laser drilled through the second conductive layer 1110 and the second substrate 1108 to expose the conductive interconnect 1106 of the trace pattern. FIG. 30E illustrates the via 1112 plated with a thick conductive via fill 1114, which may be a thick noble metal, such as Gold, to electrically connect the second conductive layer 1110 to the trace pattern. Turning to FIGS. 30F-30G, the second conductive layer 1110 is patterned and etched to form an electrode array and a connection array 1116, with an electroplate 1118 deposited thereon.

Figure 31:
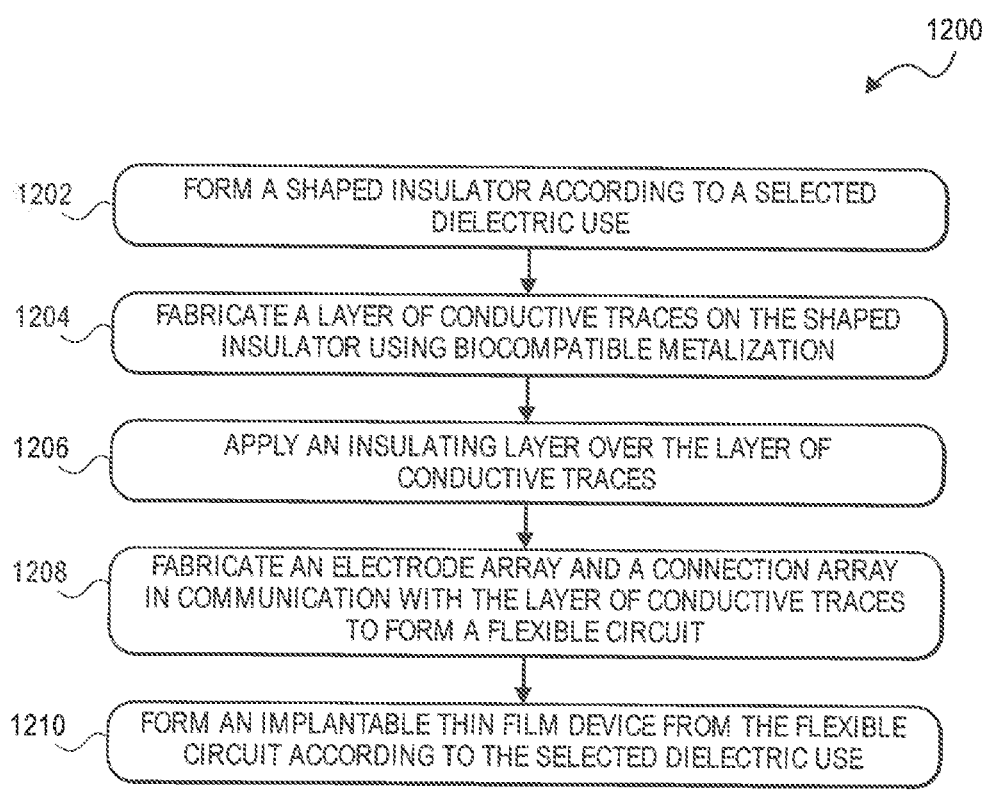
FIG. 31 illustrates example operations for manufacturing an implantable thin film device for patient treatment.

Referring to FIG. 31, example operations 1200 for manufacturing an implantable thin film device for patient treatment are shown. In one Implementation, an operation 1202 forms a shaped insulator according to a selected dielectric use, which may be, without limitation, spinal cord stimulation, deep brain stimulation, catheter ablation, cardiac rhythm management, occipital nerve stimulation, peripheral nerve stimulation, electrophysiology, vagus nerve, atrial fibrillation, and/or the like.

The shaped insulator has an inner surface and an outer surface. In one implementation, the operation 1202 forms the shaped insulator with a profile shaped according to the selected dielectric use. For example, the shaped insulator may be two-dimensional with the profile being flat, or the shaped insulator may be three-dimensional with the profile being non-flat. A non-flat profile, may be a variety of shapes, including, but not limited to, curved, angled, and/or irregular. For example, the non-flat profile may be cylindrical. As described herein, the operation 1202 may form the shaped insulator from a variety of materials adapted to withstand processing conditions involved in the application of conductive arrays and junctions as well as to withstand the biochemistry within a patient body without causing any adverse reactions. These materials may include, without limitation, polyimide, glass, ceramic, LCP, organic thermoplastic polymer, inorganic material, non-conductive oxide, thermoset polymer, and/or the like. The shaped insulator may be flexible, non-flexible, and/or transitionally stiff.

In one implementation, an operation 1204 fabricates a layer of conductive traces on the shaped insulator using biocompatible metallization. The operation 1204 may fabricate the layer of conductive traces on the inner surface of the shaped insulator. The layer of conductive traces defines a trace pattern. In one implementation, the biocompatible metallization includes metal deposition, foil attachment, and/or conductive printing using one or more conductors, such as Palladium, Gold, Titanium, Platinum, Platinum-Iridium, and/or the like. As detailed herein, the operation 1204 may define the trace pattern through ablation, etching, resist printing, conductive printing, insulative impregnation, insulative implantation, and/or the like.

An operation 1206 applies an insulating layer having an inner surface and an outer surface over the layer of conductive traces. In one Implementation, the operation 1206 applies the insulating layer with intimate contact between the inner surface of the shaped insulator and the inner surface of the insulating layer outside the trace pattern. The operation 1206 may apply the insulating layer through extrusion, coating, casting, deposition, lamination, printing, and/or the like. The insulating layer and the layer of conductive traces may be part of a multiple-layer series of alternating insulating and conducting layers.

An operation 1208 fabricates an electrode array and a connection array in electrical communication with the layer of conductive traces to form a flexible circuit. The electrode array and the connection array may be formed on at least one of the outer surface of the shaped insulator or the outer surface of the insulating layer. In one implementation, the operation 1208 forms one or more vias in at least one of the outer surface of the shaped insulator or the outer surface of the insulating layer. The vias are filled with conductive material to establish electrical communication between the electrode array and the layer of conductive traces. The flexible circuit may be a full tip-to-tail circuit having a stimulation end and a terminal end with the electrode array disposed at the stimulation end and the connection array disposed at the terminal end. The flexible circuit may be a tip assembly with the connection array electrically connected to one or more conductors of a body.

An operation 1210 forms an implantable thin film device from the flexible circuit according to the selected dielectric use. In one implementation, the operation 1210 forms the implantable thin film device by laminating the flexible circuit to a carrier, preparing the flexible circuit for deployment, wrapping the flexible circuit around a body, coiling the flexible circuit around a body, and/or the like. The implantable thin film device may be, for example, a percutaneous lead having a stimulation end and a terminal end formed from the flexible circuit. In one implementation, the connection array is configured to connect to an implantable power source.

Figure 32:
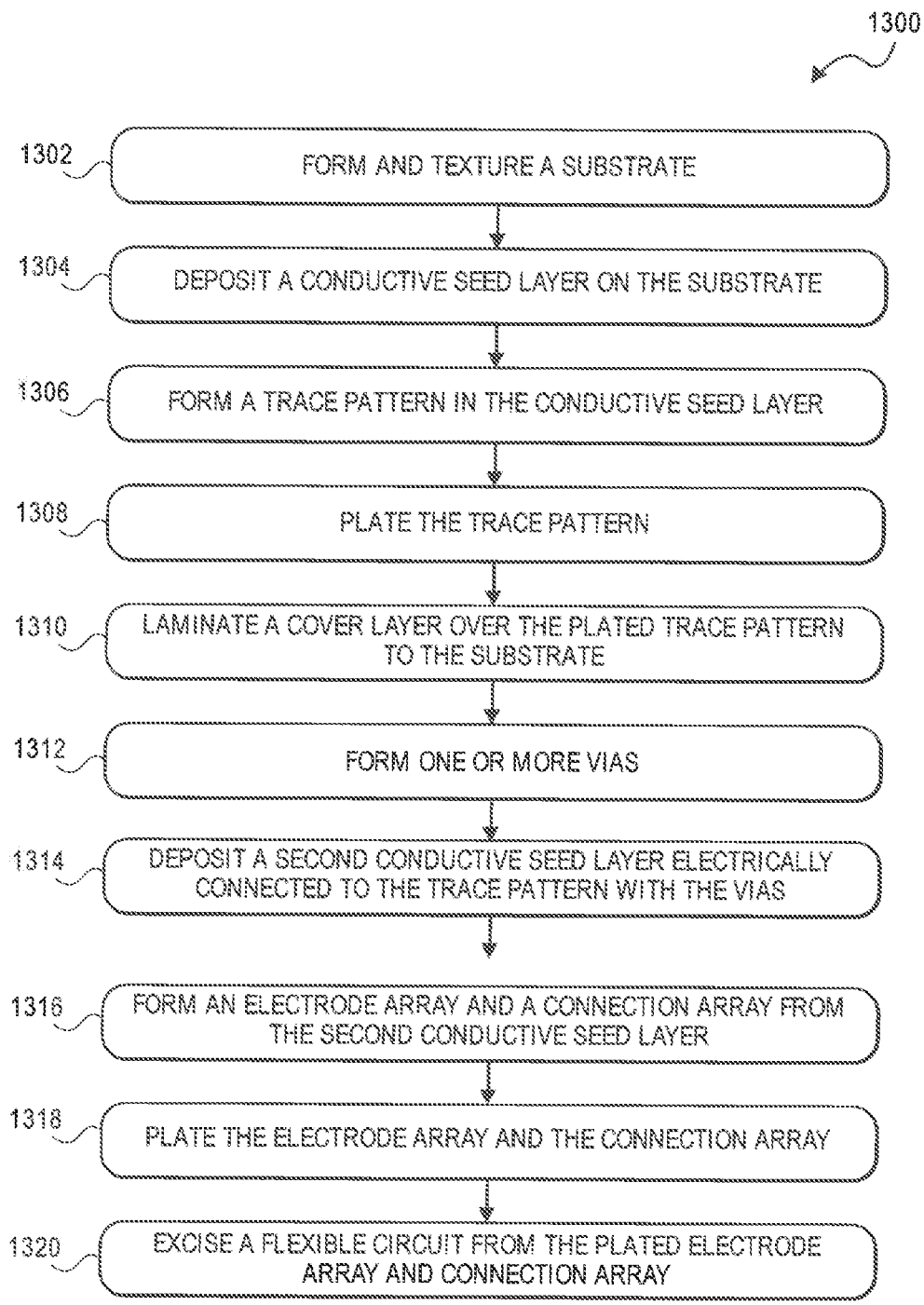
FIG. 32 illustrates example operations for forming a flexible circuit from a two-dimensional substrate.

Referring next to FIG. 32, example operations 1300 for forming a flexible circuit from a two-dimensional substrate are illustrated, in one implementation, an operation 1302 forms and textures a substrate. More particularly, in one implementation, the operation 1302 provides raw material which may be, for example, an LCP substrate or a substrate with an LCP overlay. The thickness of the layer of LCP may be approximately 10-100 microns. In one example, the LCP has a thickness of approximately 25-50 microns. The operation 1302 then textures the raw material for bonding. The raw material may be textured, for example, using $O_2$ plasma texture, Ar texture, and/or a wet texture.

In one implementation, an operation 1304 deposits a conductive seed layer on the substrate. The conductive seed layer may comprise one or more layers of biocompatible metals. In one implementation, the operation 1304 vacuum deposits two sequential layers of Ti/Au with approximately 500-5000 Angstroms of Au over approximately 100-1000 Angstroms of Ti. An operation 1306 forms a trace pattern in the conductive seed layer. In one implementation, the operation 1306 deposits resist for patterning and performs a two stage etching of wet and/or dry etching. The trace pattern formed by the operation 1306 may include final line and space from approximately 10-100 microns with a number of channels ranging from 1 to 256. An operation 1308 plates the trace pattern. In one implementation, approximately 1-15 microns of Au are plated on top of the trace pattern.

In one implementation, an operation 1310 laminates a cover layer over the plated trace pattern to the substrate. More particularly, an LCP coverlay is laminated to the trace side (i.e., the side of the substrate onto which the conductive seed layer was deposited in the operation 1304). In one implementation, the operation 1310 manages the glass transition temperature (Tg) of the cover layer and varies the Tg of the substrate to enable thermal bonding of the cover layer to the substrate without distorting the plated trace pattern.

An operation 1312 forms one or vias. In one implementation, the operation 1312 laser etches or otherwise forms the vies in the cover layer and/or the substrate. The vias may have a diameter ranging from approximately 50-500 microns. In one implementation, the operation 1312 fills the vias with a thick noble metal via fill. For example, the operation 1312 may plate Au in the vias.

An operation 1316 deposits a second conductive seed layer on the cover layer and/or the substrate. The second conductive seed layer is electrically connected to the trace pattern with the plated vias. An operation 1318 forms an electrode array and a connection array from the second conductive seed layer(s). An operation 1318 plates the electrode array and the connection array. In one implementation, the operation 1318 builds up the electrode array and the connection array by plating Au from approximately 1-15 microns to form thick Au electrode and connection arrays, and the operation 1318 plates approximately 0.5 to 5 microns of Pt or Pt—Ir over the thick Au electrode and connection arrays to form plated electrode and connection arrays. An operation 1320 excises a flexible circuit with the plated electrode and connection arrays, Stated differently the operations 1302-1320 form a full tip-to-tail, fully biocompatible flexible circuit lead with in situ fully formed traces, electrodes, and contacts. The flexible circuit uses a thick noble metal plate up to form traces that may be greater than approximately 12 inches or otherwise sized and shaped for a selected dielectric use. Similarly, the flexible circuit uses thick noble metal via fill. The flexible circuit includes full electrodes and contacts adapted for connection with a power source without further mechanical and/or metal components, such as attachments, bonds, welds, and/or the like.

Figure 33:
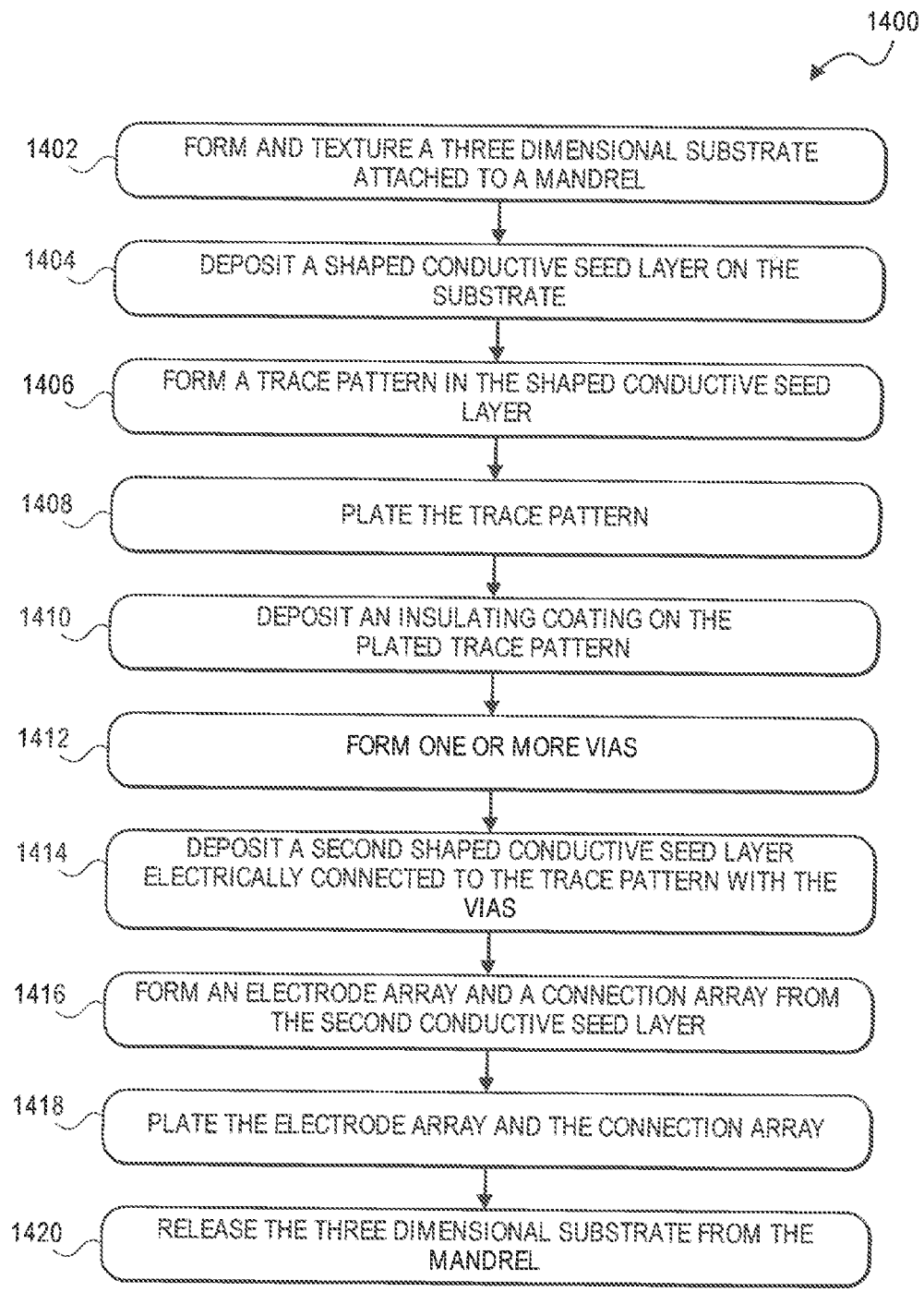
FIG. 33 illustrates example operations for manufacturing an implantable thin film device from a three-dimensional substrate.

FIG. 33 illustrates example operations 1400 for manufacturing an implantable thin film device from a three-dimensional substrate. In one implementation, an operation 1402 forms and texture a three-dimensional substrate attached to a mandrel. More particularly, the operation 1402 forms or otherwise provides raw material in the form of a polyimide tube. In one implementation, the polyimide tube has an outer diameter of approximately 30-100 thousandths of an inch and a tube wall of approximately 1-10 thousandths of an inch. The polyimide tube is attached to the mandrel, which may be a Teflon coated stainless steel mandrel. The operation 1402 textures the raw material with a plasma and/or a wet process.

An operation 1404 deposits a shaped (e.g., cylindrical) conductive seed layer on the substrate. In one implementation, the operation 1404 blanket vapor deposits a Ti/Au conductive seed layer around an entirety of the polyimide tube with approximately 500-5000 Angstroms of Au over approximately 100-1000 Angstroms of Ti. An operation 1406 forms a trace pattern in the shaped conductive seed layer. In one implementation, the operation 1406 uses a three-dimensional inject process to print patterned resist onto the shaped conductive seed layer, and the operation 1406 etches the shaped conductive seed layer using a wet/dry etch process or a wet/wet etch process. In another implementation, the operation 1406 laser ablates the shaped conductive seed layer into the trace pattern. An operation 1408 plates the trace pattern. In one implementation, the operation 1408 builds up the traces with a thick Au plate of approximately 1-15 microns.

An operation 1410 deposits an insulating coating on the plated trace pattern. In one implementation, the operation 1410 dip coats or vapor deposits the insulating coating, which may be a polymer coating, on the plated trace pattern. An operation 1412 forms one or more vias. In one implementation, the operation 1412 laser ablates or otherwise forms the vies in the insulating coating. In one implementation, the operation 1412 fills the vias with a thick noble metal via fill. For example, the operation 1412 may plate Au in the vias.

An operation 1414 deposits a second shaped conductive seed layer electrically connected to the trace pattern with the vias. In one implementation, the operation 1414 blanket vapor deposits the second shaped conductive seed layer of Ti/Au. An operation 1416 forms an electrode array and a connection array from the second conductive seed layer. In one implementation, the operation 1416 patterns the second shaped conductive seed layer using a three-dimensional inject process to print patterned resist onto the second shaped conductive seed layer, and the operation 1416 etches the second shaped conductive seed layer using a wet/dry or wet/wet etch process. In another implementation, the operation 1416 laser ablates the second shaped conductive seed layer into the electrode array and the connection array. An operation 1418 plates the electrode array and the connection array, for example, with a thick noble metal plate, such as an Au plate of approximately 1-15 microns. An operation 1420 releases the three dimensional substrate from the mandrel providing an implantable thin film device with a flexible circuit that may be connected directly into a power source.

Various other modifications and additions can be made to the exemplary implementations discussed without departing from the spirit and scope of the presently disclosed technology. For example, while the embodiments described above refer to particular features, the scope of this disclosure also includes implementations having different combinations of features and implementations that do not include all of the described features. Accordingly, the scope of the presently disclosed technology is intended to embrace all such alternatives, modifications, and variations together with all equivalents thereof.

What is claimed is:

1. An implantable thin film stimulation device formed as a circuit tip assembly, comprising:
   a shaped insulator having an inner surface and an outer surface, the shaped insulator having a non-flat profile, the shaped insulator further having a stimulation end and a terminal end;
   a layer of conductive traces disposed on the inner surface of the shaped insulator and defining a trace pattern, wherein the layer of conductive traces is fabricated on the inner surface of the shaped insulator using biocompatible metallization;
   an insulating layer having an outer surface and an inner surface, the insulating layer applied over the layer of conductive traces;
   an electrode array having one or more electrodes positioned at the stimulation end of the shaped insulator; and
   a connection array having one or more connection spots disposed at the terminal end of the shaped insulator, the electrode array and the connection array arranged in electrical communication with the layer of conductive traces to form at least a portion of a body of the circuit tip assembly.

2. The implantable thin film stimulation device of claim 1, wherein an electrical connection between the connection array and the layer of conductive traces is established through one or more vias filled with conductive material, the one or more vias formed at the terminal end in at least one of the shaped insulator or in the insulating layer.

3. The implantable thin film stimulation device of claim 2, wherein the shaped insulator comprises a three-dimensional insulator formed as a tubular structure having the non-flat profile.

4. The implantable thin film stimulation device of claim 3, wherein the non-flat profile of the three-dimensional insulator comprises a curved profile for defining a cylindrically shaped substrate of the tubular structure.

5. The implantable thin film stimulation device of claim 3, wherein the non-flat profile of the three-dimensional insulator comprises one of an angled profile and an irregular profile for defining an angularly or irregularly shaped elongated substrate of the tubular structure.

6. The implantable thin film stimulation device of claim 3, wherein the three-dimensional insulator formed as one of a flexible substrate, a transitionally stiff substrate, and a rigid substrate.

7. The implantable thin film stimulation device of claim 3, wherein the trace pattern extends along the body of the circuit tip assembly between the stimulation end and the terminal end, the trace pattern formed using at least one of resist printing, laser ablation, etching, and conductive printing, involving a suitable biocompatible conductive material.

8. The implantable thin film stimulation device of claim 3, wherein the trace pattern comprises a stimulation end trace portion, a terminal end trace portion and a body trace portion electrically disposed between the stimulation end trace portion and the terminal end trace portion.

9. The implantable thin film stimulation device of claim 8, wherein at least one of the stimulation end trace portion, the terminal end trace portion and the body trace portion comprises at least one of a helix pattern, a zig-zag pattern, an angled pattern, and a contoured pattern.

10. The implantable thin film stimulation device of claim 3, wherein the non-flat profile of the shaped insulator is defined transverse to a length of the shaped insulator, the non-flat profile shaped according to a selected dielectric use based on parameters comprising at least one of a stimulation direction, stimulation surface area, migration likelihood of the circuit tip assembly after implant, type of stimulation therapy application, and a surgical deployment technique to be used for a patient.

11. The implantable thin film stimulation device of claim 3, wherein the one or more electrodes of the electrode array or the one or more connection spots of the connection array comprise three-dimensional shapes.

12. A method of manufacturing a circuit tip assembly operative as an implantable thin film stimulation device for patient treatment, the method comprising:
    forming a shaped insulator having an inner surface and an outer surface, the shaped insulator having a non-flat profile, the shaped insulator further having a stimulation end and a terminal end;
    forming a layer of conductive traces disposed on the inner surface of the shaped insulator and defining a trace pattern using biocompatible metallization;
    forming an insulating layer having an outer surface and an inner surface, the insulating layer applied over the layer of conductive traces;
    forming an electrode array of one or more electrodes positioned at the stimulation end of the shaped insulator; and
    forming a connection array of one or more connection spots positioned at the terminal end of the shaped insulator, the electrode array and the connection array arranged in electrical communication with the layer of conductive traces to form at least a portion of a body of the circuit tip assembly.

13. The method of claim 12, further comprising:
    forming one or more vias at the terminal end in at least one of the shaped insulator or in the insulating layer; and
    forming an electrical connection between the connection array and the layer of conductive traces through the one or more vias filled with conductive material.

14. The method of claim 13, wherein the shaped insulator is formed as a three-dimensional insulator comprising a tubular structure having the non-flat profile.

15. The method of claim 14, wherein the non-flat profile of the three-dimensional insulator comprises a curved profile for defining a cylindrically shaped substrate of the tubular structure.

16. The method of claim 14, wherein the non-flat profile of the three-dimensional insulator comprises one of an angled profile and an irregular profile for defining an angularly or irregularly shaped elongated substrate of the tubular structure.

17. The method of claim 14, wherein the three-dimensional insulator formed as one of a flexible substrate, a transitionally stiff substrate, and a rigid substrate.

18. The method of claim 14, wherein the trace pattern is formed to extend along the body of the circuit tip assembly between the stimulation end and the terminal end, the trace pattern formed using at least one of resist printing, laser ablation, etching, and conductive printing, involving a suitable biocompatible conductive material.

19. The method of claim 14, wherein the trace pattern comprises a stimulation end trace portion, a terminal end trace portion and a body trace portion electrically disposed between the stimulation end trace portion and the terminal end trace portion.

20. The method of claim 19, wherein at least one of the stimulation end trace portion, the terminal end trace portion and the body trace portion is formed as one of a helix pattern, a zig-zag pattern, an angled pattern and a contoured pattern.

21. The method of claim 14, wherein the non-flat profile of the shaped insulator is defined transverse to a length of the shaped insulator, the non-flat profile shaped according to a selected dielectric use based on parameters comprising at least one of a stimulation direction, stimulation surface area, migration likelihood of the circuit tip assembly after implant, type of stimulation therapy application, and a surgical deployment technique to be used for a patient.

22. The method of claim 14, wherein the one or more electrodes of the electrode array or the one or more connection spots of the connection array are formed to comprise three-dimensional shapes.

* * * * *

UNITED STATES PATENT AND TRADEMARK OFFICE
CERTIFICATE OF CORRECTION

| | | |
|---|---|---|
| PATENT NO. | : 11,191,952 B2 | Page 1 of 1 |
| APPLICATION NO. | : 16/278464 | |
| DATED | : December 7, 2021 | |
| INVENTOR(S) | : John R. Gonzalez et al. | |

It is certified that error appears in the above-identified patent and that said Letters Patent is hereby corrected as shown below:

In the Specification

At Column 4, Line number 50, delete "Implanted" and replace with --implanted--.
At Column 5, Line number 12, delete "hi" and replace with --in--.
At Column 6, Line number 62, delete "pattern, in" and replace with --pattern. In--.
At Column 8, Line number 4, delete "device 60" and replace with --device 80--.
At Column 8, Line number 27, delete "hi" and replace with --in--.
At Column 8, Line number 43, delete "terminal/end" and replace with --terminal end--.
At Column 8, Line number 66, delete "Ups" and replace with --tips--.
At Column 9, Line number 32, delete "dead" and replace with --lead--.
At Column 10, Line number 44, delete "wire 188" and replace with --wire 108--.
At Column 11, Line number 35, delete "DSB" and replace with --DBS--.
At Column 13, Line number 9, delete "Insulator" and replace with --insulator--.
At Column 13, Line number 35, delete "Insulating" and replace with --insulating--.
At Column 13, Line number 67, delete "608" and replace with --606--.
At Column 14, Line number 39, delete "616" and replace with --618--.
At Column 14, Line number 53, delete "DSB" and replace with --DBS--.
At Column 15, Line number 15, delete "vies" and replace with --vias--.
At Column 16, Line number 28, delete "lube" and replace with --tube--.
At Column 18, Line number 40, delete "FIG. 308" and replace with --FIG. 30B--.
At Column 18, Line number 64, delete "Implementation" and replace with --implementation--.
At Column 19, Line number 10, delete "profile, may" and replace with --profile may--.
At Column 19, Line number 38, delete "Implementation" and replace with --implementation--.
At Column 20, Line number 11, delete "illustrated, in" and replace with --illustrated. In--.
At Column 20, Line number 47, delete "vies" and replace with --vias--.
At Column 20, Line number 66, delete "arrays, Stated" and replace with --arrays. Stated--.
At Column 21, Line number 46, delete "vies" and replace with --vias--.

Signed and Sealed this
Eighth Day of February, 2022

Drew Hirshfeld
*Performing the Functions and Duties of the
Under Secretary of Commerce for Intellectual Property and
Director of the United States Patent and Trademark Office*